United States Patent [19]

Finke et al.

[11] Patent Number: 5,719,149
[45] Date of Patent: Feb. 17, 1998

[54] MORPHOLINE DERIVATIVES AND THEIR USE AS THERAPEUTIC AGENTS

[75] Inventors: Paul Finke, Milltown, N.J.; Timothy Harrison, Great Dunmow, United Kingdom; Richard Thomas Lewis; Angus Murray MacLeod, both of Bishops Stortford, United Kingdom; Andrew Pate Owens, Ellington Thorpe, United Kingdom

[73] Assignee: Merck Sharp & Dohme Ltd., Hoddesdon, England

[21] Appl. No.: 793,573

[22] PCT Filed: Aug. 30, 1995

[86] PCT No.: PCT/GB95/02039

§ 371 Date: Feb. 27, 1997

§ 102(e) Date: Feb. 27, 1997

[87] PCT Pub. No.: WO96/07649

PCT Pub. Date: Mar. 14, 1996

[30] Foreign Application Priority Data

Sep. 2, 1994 [GB] United Kingdom .................. 9417956

[51] Int. Cl.⁶ .................. A61K 31/535; C07D 265/32; C07D 413/06
[52] U.S. Cl. .................. 514/231.8; 514/235.3; 544/70; 544/87; 544/129; 544/141
[58] Field of Search .................. 544/70, 87, 129, 544/141; 514/231.8

[56] References Cited

U.S. PATENT DOCUMENTS 5,612,337 3/1997 Baker et al. .................. 514/236.2

FOREIGN PATENT DOCUMENTS

| 0 528 495 | 2/1993 | European Pat. Off. . |
|---|---|---|
| 0 577 394 | 1/1994 | European Pat. Off. . |
| WO 95/16679 | 6/1995 | WIPO . |
| WO 95/18124 | 7/1995 | WIPO . |

Primary Examiner—Robert W. Ramsuer
Attorney, Agent, or Firm—J. Eric Thies; David L. Rose

[57] ABSTRACT

The present invention relates to compounds of formula (I) wherein: $R^1$, $R^2$, $R^3$, $R^4$ and $R^5$ are selected from a variety of suitable aromatic substituents; $R^6$ is hydrogen, $C_{1-6}$alkyl, $C_{3-7}$cycloalkyl, $C_{3-7}$cycloalkylC$_{1-4}$alkyl, phenyl, or $C_{2-4}$alkyl substituted by $C_{1-4}$alkoxy or hydroxy; $R^7$ is hydrogen, $C_{1-6}$alkyl, $C_{3-7}$cycloalkyl, $C_{3-7}$cycloalkylC$_{1-4}$alkyl, phenyl, $C_{2-4}$alkyl substituted by $C_{1-4}$alkoxy or hydroxy, or the group $C(=NR^c)NR^aR^b$; or $R^6$ and $R^7$, together with the nitrogen atom to which they are attached, form an optionally substituted saturated heterocyclic ring of 4 to 7 ring atoms which may optionally contain in the ring one oxygen or sulphur atom or a group selected from $NR^8$, $S(O)$ or $S(O)_2$; or $R^6$ and $R^7$, together with the nitrogen atom to which they are attached, form a piperidino ring substituted by a spiro-fused indene or indoline group, each of which may be unsubstituted or substituted; $R^8$ is hydrogen, $C_{1-4}$alkyl, hydroxyC$_{1-4}$alkyl or $C_{1-4}$alkoxyC$_{1-4}$alkyl; $R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring; X is selected from —CH$_2$CH$_2$—, —COCH$_2$— or —CH$_2$CO—; and Y is hydrogen, or $C_{1-4}$alkyl optionally substituted by a hydroxyl group; or a pharmaceutically acceptable salt thereof. The compounds are of particular use in the treatment or prevention of pain, inflammation, migraine, emesis and postherpetic neuralgia.

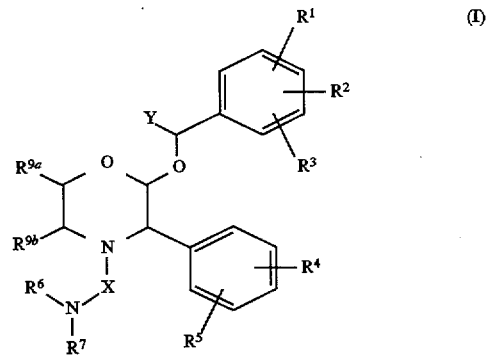

15 Claims, No Drawings

MORPHOLINE DERIVATIVES AND THEIR USE AS THERAPEUTIC AGENTS

This application is a 371 of PCT/GB95/02039 filed Aug. 30, 1995.

This invention relates to a class of morpholine derivatives which are useful as tachykinin antagonists.

The tachykinins are a group of naturally occurring peptides found widely distributed throughout mammalian tissues, both within the central nervous system and in peripheral nervous and circulatory systems.

At present, there are three known mammalian tachykinins referred to as substance P, neurokinin A (NKA, substance K, neuromedin L) and neurokinin B (NKB, neuromedin K (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations (Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" TIPS (1987) 8, 506–510), specifically in the transmission of pain in migraine (Sandberg et al, *J. Med. Chem.*, (1982) 25, 1009) and in arthritis (Levine et al in *Science* (1984) 226, 547–549). Tachykinins have also been implicated in gastrointestinal (GI) disorders and diseases of the GI tract such as inflammatory bowel disease (Mantyh et al in *Neuroscience* (1988) 25(3), 817–837 and D. Regoli in "Trends in Cluster Headache" Ed. Sicuteri et al, Elsevier Scientific Publishers, Amsterdam (1987) page 85–95) and emesis (F. D. Tattersall et al, *Eur. J. Pharmacol.*, (1993) 250, R5-R6). It is also hypothesised that there is a neurogenic mechanism for arthritis in which substance P may play a role (Kidd et al "A Neurogenic Mechanism for Symmetrical Arthritis" in *The Lancet*, Nov. 11, 1989 and Grönblad et al, "Neuropeptides in Synovium of Patients with Rheumatoid Arthritis and Osteoarthritis" in *J. Rheumatol.* (1988) 15(12), 1807–1810). Therefore, substance P is believed to be involved in the inflammatory response in diseases such as rheumatoid arthritis and osteoarthritis, and fibrositis (O'Byrne et al, *Arthritis and Rheumatism* (1990) 33, 1023–1028). Substance P antagonists alone or in combination with bradykinin receptor antagonists may also be useful in the prevention and treatment of inflammatory conditions in the lower urinary tract, especially cystitis (Giuliani et al, *J. Urology* (1993) 150, 1014–1017). Other disease areas where tachykinin antagonists are believed to be useful are allergic conditions (Hamelet et al, *Can. J. Pharmacol. Physiol.* (1988) 66, 1361–1367), immunoregulation (Lotz et al, *Science* (1988) 241, 1218–1221; Kimball et al, *J. Immunol.* (1988) 141(10), 3564–3569 and Perianin et al, *Biochem. Biophys. Res. Commun.* (1989) 161, 520), post-operative pain and nausea (Bountra et al, *Eur. J. Pharmacol.* (1993) 249, R3-R4 and Tattersall et al, *Neuropharmacology* (1994) 33, 259–260), vasodilation, bronchospasm, reflex or neuronal control of the viscera (Mantyh et al, PNAS (1988) 85, 3235–3239) and, possibly by arresting or slowing β-amyloid-mediated neurodegenerative changes (Yankner et al, *Science* (1990) 250, 279–282) in senile dementia of the Alzheimer type, Alzheimer's disease and Down's Syndrome.

Tachykinin antagonists may also be useful in the treatment of small cell carcinomas, in particular small cell lung cancer (SCLC). (Langdon et al, *Cancer Research* (1992) 52, 4554–7).

Substance P may also play a role in demyelinating diseases such as multiple sclerosis and amyotrophic lateral sclerosis (Luber-Narod et al, poster C.I.N.P. XVIIIth Congress, June 28th–July 2nd, 1992), and in disorders of bladder function such as bladder detrusor hyper-reflexia (*The Lancet*, May 16th, 1992, 1239). Antagonists selective for the NK-1 and/or NK-2 receptor may be useful in the treatment of asthmatic disease (Frossard et al, *Life Sci.* (1991) 49, 1941–1953; Advenier et al, *Biochem. Biophys. Res. Commun.* (1992) 184(3), 1418–1424; and Barnes et al, TIPS (1993) 11, 185–189).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

Substance P antagonists may also be useful in mediating neurogenic mucus secretion in mammalian airways and hence provide treatment and symptomatic relief in diseases characterized by mucus secretion, in particular, cystic fibrosis (see Ramnarine et al, abstract presented at 1993 ALA/ATS International Conference, May 16–19, 1993, published in *Am. Rev. Resp. Dis.* (May 1993)).

European patent specification no. 0 577 394 (published Jan. 5th, 1994) discloses morpholine and thiomorpholine tachykinin receptor antagonists of the general formula

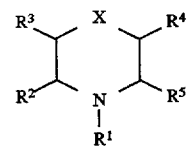

wherein $R^1$ is a large variety of substituents;
$R^2$ and $R^3$ are inter alia hydrogen;

$R^4$ is inter alia

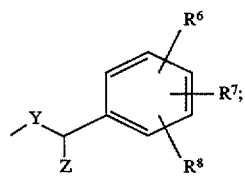

$R^5$ is inter alia optionally substituted phenyl;
$R^6$, $R^7$ and $R^8$ are a variety of substituents;
X is O, S, SO or $SO_2$;
Y is inter alia O; and
Z is hydrogen or $C_{1-4}$alkyl.

We have now found a further class of non-peptides which are potent antagonists of tachykinins, especially of substance P.

It is desirable that compounds may be administered orally and by injection. Certain compounds have now been discovered which act as potent non-peptide tachykinin antagonists and which, by virtue of their advantageous aqueous solubility, are particularly easily formulated for administration by both the oral and injection routes, for example in aqueous media.

The present invention provides compounds of the formula (I):

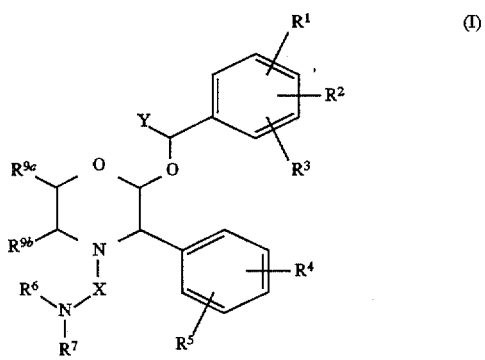

wherein
$R^1$ is hydrogen, halogen, $C_{1-6}$alkyl, $C_{1-6}$alkoxy, $CF_3$, $NO_2$, CN, $CO_2R^a$, $CONR^aR^b$, $C_{2-6}$alkenyl, $C_{2-6}$alkynyl or $C_{1-4}$alkyl substituted by $C_{1-4}$alkoxy, and wherein $R^a$ and $R^b$ are each independently hydrogen or $C_{1-4}$alkyl;

$R^2$ is hydrogen, halogen, $C_{1-6}$alkyl, $C_{1-6}$alkoxy substituted by $C_{1-4}$alkoxy or $CF_3$;

$R^3$ is hydrogen, halogen or $CF_3$;

$R^4$ is hydrogen, halogen, $C_{1-6}$alkyl, $C_{1-6}$alkoxy, hydroxy, $CF_3$, $NO_2$, CN, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, $C_{1-6}$alkoxy substituted by $C_{1-4}$alkoxy or $CF_3$;

$R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

$R^7$ is hydrogen, $C_{1-6}$alkyl, $C_{3-7}$cycloalkyl, $C_{3-7}$cycloalkyl$C_{1-4}$alkyl, phenyl, $C_{2-4}$alkyl substituted by $C_{1-4}$alkoxy or hydroxy, or the group $C(=NR^c)NR^aR^b$, where $R^a$ and $R^b$ are as previously defined and $R^c$ is hydrogen, $C_{1-6}$alkyl, CN or $COR^a$;

or $R^6$ and $R^7$, together with the nitrogen atom to which they are attached, form a saturated heterocyclic ring of 4 to 7 ring atoms which may optionally contain in the ring one oxygen or sulphur atom or a group selected from $NR^8$, S(O) or $S(O)_2$ and which ring may be optionally substituted by one or two groups selected from phenyl, benzyl, hydroxy$C_{1-4}$alkyl, $C_{1-4}$alkoxy$C_{1-4}$alkyl, hydroxy, oxo, $COR^a$ or $CO_2R^a$ where $R^a$ is as previously defined;

or $R^6$ and $R^7$, together with the nitrogen atom to which they are attached, form a piperidino ring substituted by a spiro-fused indene or indoline group, each of which may be unsubstituted or substituted on any available carbon atom by a group selected from $C_{1-6}$alkyl, $C_{1-6}$alkoxy, hydroxy, halogen, cyano, trifluoromethyl, $SO_2C_{1-6}$alkyl, $NR^aR^b$, $NR^aCOR^b$ or $CONR^aR^b$; or, in the case of an indoline group, on the nitrogen atom by a group selected from $C_{1-6}$alkyl, $C_{3-7}$cycloalkyl, $C_{3-7}$cycloalkyl$C_{1-4}$alkyl, phenyl$C_{1-4}$alkyl, $CO_2R^a$, $CONR^aR^b$, $SOR^a$ or $SO_2R^a$, where $R^a$ and $R^b$ are as previously defined;

$R^8$ is hydrogen, $C_{1-4}$alkyl, hydroxy$C_{1-4}$alkyl or $C_{1-4}$alkoxy$C_{1-4}$alkyl;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

x is selected from $-CH_2CH_2-$, $-COCH_2-$ or $-CH_2CO-$; and

Y is hydrogen, or $C_{1-4}$alkyl optionally substituted by a hydroxyl group;

and pharmaceutically acceptable salts thereof.

A preferred class of compounds of formula (I) is that wherein $R^1$ is hydrogen, $C_{1-4}$alkyl, $C_{1-4}$alkoxy, halogen or $CF_3$.

Another preferred class of compounds of formula (I) is that wherein $R^2$ is hydrogen, $C_{1-4}$alkyl, $C_{1-4}$alkoxy, halogen or $CF_3$.

Also preferred is the class of compounds of formula (I) wherein $R^3$ is hydrogen, fluorine, chlorine or $CF_3$.

A particularly preferred class of compounds of formula (I) is that wherein $R^1$ is hydrogen, fluorine, chlorine or $CF_3$.

Another particularly preferred class of compounds of formula (I) is that wherein $R^2$ is fluorine, chlorine or $CF_3$.

Also particularly preferred is the class of compounds of formula (I) wherein $R^3$ is hydrogen, fluorine, chlorine or $CF_3$.

Preferably $R^4$ and $R^2$ are in the 3 and 5 positions of the phenyl ring.

More preferably $R^1$ is hydrogen, 3-fluoro or 3-$CF_3$.
More preferably $R^2$ is 5-fluoro or 5-$CF_3$.
More preferably $R^3$ is hydrogen.
Most preferably $R^1$ is H, 3-F or 3-$CF_3$, $R^2$ is 5-$CF_3$ and $R^3$ is hydrogen.

A further preferred class of compound of formula (I) is that wherein $R^4$ is hydrogen.

Another preferred class of compounds of formula (I) is that wherein $R^5$ is hydrogen, fluorine, chlorine or $CF_3$.

Preferably $R^4$ is hydrogen and $R^5$ is hydrogen or 4-fluoro.

Yet another preferred class of compounds of formula (i) is that wherein $R^6$ represents hydrogen or $C_{1-6}$alkyl.

A yet further preferred class of compounds of formula (I) is that wherein $R^7$ represents hydrogen, $C_{1-6}$alkyl or the group $C(=NR^c)NR^aR^b$ wherein $R^a$, $R^b$ and $R^c$ are as previously defined.

Also preferred is the class of compounds of formula (I) wherein $R^6$ and $R^7$, together with the nitrogen atom to which they are attached, form a saturated heterocyclic ring of 4 to 7 ring atoms which may optionally contain in the ring one oxygen or sulphur atom or a group selected from $NR^8$, S(O) or $S(O)_2$ and which ring may be optionally substituted by phenyl, benzyl, hydroxy$C_{1-4}$alkyl, $C_{1-4}$alkoxy$C_{1-4}$alkyl, hydroxy, oxo, $COR^a$ or $CO_2R^a$, or wherein $R^6$ and $R^7$, together with the nitrogen atom to which they are attached, form a piperidino ring substituted by a spiro-fused indene or indoline group which may be unsubstituted or substituted as previously defined.

A particularly preferred class of compounds of formula (I) is that wherein $R^6$ and $R^7$, together with the nitrogen atom to which they are attached, form a saturated heterocyclic ring of 5 or 6 ring atoms which may optionally contain in the ring one oxygen atom and which ring may be optionally substituted by phenyl, benzyl, hydroxy$C_{1-4}$alkyl, oxo or $CO_2R^a$, or wherein $R^6$ and $R^7$, together with the nitrogen atom to which they are attached, form a piperidino ring substituted by a spiro-fused indene or indoline group which may be unsubstituted or, in the case of an idoline group, substituted on the nitrogen atom by the group $SO_2R^a$, particularly $SO_2C_{1-6}$alkyl, especially $SO_2CH_3$.

In particular, the group $NR^6R^7$ preferably represents $NH_2$, $NHCH_3$, $N(CH_3)_2$, $NHC(=NCO_2R^a)NH_2$, morpholino or optionally substituted pyrrolidino or piperidino.

Where the group $NR^6R^7$ represents a piperidino ring substituted by a spiro-fused indene or indoline group the point of attachment is preferably at the 4-position of the piperidino ring through the 3-position of the indene or indoline ring. The indene or indoline ring is preferably unsubstituted or, in the case of the indoline ring, substituted on the nitrogen atom by the group $SO_2R^a$ where $R^a$ is preferably $C_{1-6}$alkyl, especially methyl.

Also preferred is the class of compounds of formula (I) wherein $R^{9a}$ and $R^{9b}$ are each independently hydrogen or methyl. Preferably $R^{9a}$ is hydrogen. Preferably $R^{9b}$ is hydrogen. Most preferably $R^{9a}$ and $R^{9b}$ are both hydrogen.

From the foregoing it will be appreciated that a particularly apt sub-group of compounds of this invention are those of the formula (Ia) and pharmaceutically acceptable salts thereof:

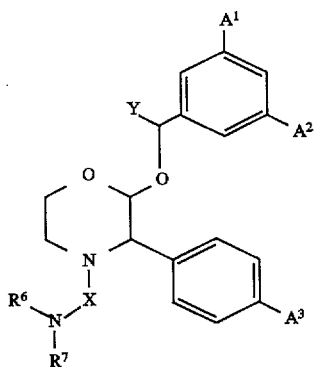
(Ia)

wherein
$A^1$ is hydrogen, fluorine or $CF_3$;
$A^2$ is fluorine or $CF_3$;
$A^3$ is fluorine or hydrogen;
and X, Y, $R^6$ and $R^7$ are as defined in relation to formula (I).

A preferred chain X for compounds of formula (I) or (Ia) is the —$CH_2CH_2$— group, or —$COCH_2$— group where the carbonyl moiety is adjacent to the morpholine ring shown in formulae (I) and (Ia). Particularly preferred is the —$CH_2CH_2$— group.

A preferred group Y for compounds of the formulae (I) or (Ia) is the methyl or $CH_2OH$ group.

Where the group $NR^6R^7$ forms a saturated heterocylic ring of 4 to 7 ring atoms which may optionally contain in the ring one oxygen or sulphur atom or a group selected from $NR^8$, $S(O)$ or $S(O)_2$, suitable heterocylic groups include azetidinyl, pyrrolidino, piperidino, homopiperidino, piperazino, N-methylpiperazino, morpholino and thiomorpholino.

Where the group $NR^6R^7$ forms a piperidino ring substituted by a spiro-fused indene or indoline group, suitable groups include

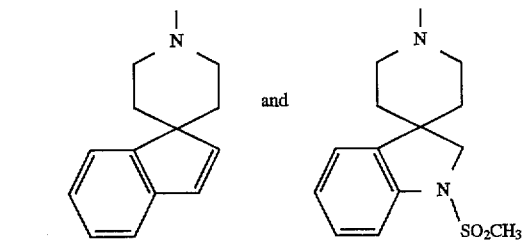

Suitable substituents on the saturated heterocyclic ring include $CH_2OH$, $CH_2OCH_3$, oxo, CHO, $CO_2H$, $CO_2CH_3$, and $CO_2CH_2CH_3$.

When used herein the term "halogen" means fluorine, chlorine, bromine and iodine. The most apt halogen are fluorine and chlorine of which fluorine is preferred.

When used herein the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The term "alkenyl" as a group or part of a group means that the group is straight or branched and contains at least one double bond. Examples of suitable alkenyl groups include vinyl and allyl.

The term "alkynyl" as a group or part of a group means that the group is straight or branched and contains at least one triple bond. An example of a suitable alkynyl group is propargyl.

Suitable cycloalkyl and cycloalkyl-alkyl groups include cyclopropyl, cyclobutyl, cyclopentyl, cyclohexyl, cyclopropylmethyl and cyclobutylmethyl.

Specific compounds within the scope of this invention include
4-(2-aminoethyl)-2-(R)-(1-(R)-(3,5-bis(trifluoromethyl)phenyl)ethoxy)-3-(S)-(4-fluorophenyl)morpholine;
2-(R)-(1-(R)-(3,5-bis(trifluoromethyl)phenyl)ethoxy)-3-(S)-(4-fluorophenyl)-(2-pyrrolidinoethyl)morpholine;
2-(R)-(1-(R)-(3,5-bis(trifluoromethyl)phenyl)ethoxy)-3-(S)-(4-fluorophenyl)-(2-morpholinoethyl)morpholine;
2-(R)-(1-(R)-(3,5-bis(trifluoromethyl)phenyl)ethoxy)-4-(2-(2'-(S)-carboxypyrrolidino)ethyl)-3-(S)-(4-fluorophenyl)morpholine;
2-(R)-(1-(R)-(3,5-bis(trifluoromethyl)phenyl)ethoxy)-3-(S)-(4-fluorophenyl)-4-(2-(2'-(R)-hydroxymethylpyrrolidino)ethyl)morpholine;
2-(R)-(1-(R)-(3,5-bis(trifluoromethyl)phenyl)ethoxy)-4-(2-(4'-carbomethoxy-2'-oxopyrrolidino)ethyl)-3-(S)-(4-fluorophenyl)morpholine;
2-(R)-(1-R)-(3,5-bis(trifluoromethyl)phenyl)ethoxy)-4-(2-(N'-carboethoxy)-guanidino)ethyl)-3-(S)-(4-fluorophenyl)morpholine;
2-(R)-(1-(R)-(3,5-bis(trifluoromethyl)phenyl)ethoxy)-3-(S)-phenyl-4-(2-(4-phenylpiperidino)ethyl)morpholine;
3-(S)-phenyl-4-(2-(4-phenylpiperidino)ethyl)-2-(R)-(1-(R)-(3-(trifluoromethyl)phenyl)ethoxy)morpholine;
2-(R)-(1-(R)-(3-fluoro-5-(trifluoromethyl)phenyl)ethoxy)-3-(S)-phenyl-4-(2-(spiro(indene-3',4-piperidino))ethyl)morpholine;
2-(R)-(1-(R)-(3-fluoro-5-(trifluoromethyl)phenyl)ethoxy)-3-(S)-phenyl-4-(2-(4-phenylpiperidino)ethyl)morpholine;

2-(R)-(1- (R)-(3 -fluoro-5-(trifluoromethyl)phenyl)ethoxy) -4-(2 -( 1 '-methylsulfonyl-spiro(indoline-3',4-piperidino) )ethyl)-3-(S)-phenylmorpholine;

2-(R)-(1-(R)-(3-fluoro-5-(trifluoromethyl)phenyl)ethoxy)- 3-(S)-phenyl-4-(2-(4-piperidino)ethyl)morpholine;

2-(S)-(3,5-bis(trifluoromethyl)phenyl)methyloxy)-3-(S)- phenyl-4-(2 -(4-phenylpiperidino)ethyl)morpholine;

4-(2-(4-benzylpiperidino)ethyl)-2-(S)-(3,5-bis (trifluoromethyl)phenyl)-methyloxy)-3-(S)- phenylmorpholine;

and pharmaceutically acceptable salts thereof.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts such as those formed with hydrochloric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The pharmaceutically acceptable salts of the present invention may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention have at least three asymmetric centres, and may accordingly exist both as enantiomers and as diastereoisomers. It is to be understood that all such isomers and mixtures thereof are encompassed within the scope of the present invention.

The preferred compounds of the formula (I), and (Ia) will have the 2- and 3-substituent cis and the preferred stereochemistry at the 2-position is that possessed by the compound of Example 1 (i.e. 2-(R)-), the preferred stereochemistry of the 3-position is that possessed by the compound of Example 1 (i.e. 3-(S)), and the preferred stereochemistry of the carbon to which the group Y is attached is either (R) when Y is $C_{1-4}$alkyl (e.g. methyl) or (S) when Y is $C_{1-4}$alkyl substituted by a hydroxy group (e.g. hydroxymethyl). Thus for example as shown in formula (Ib)

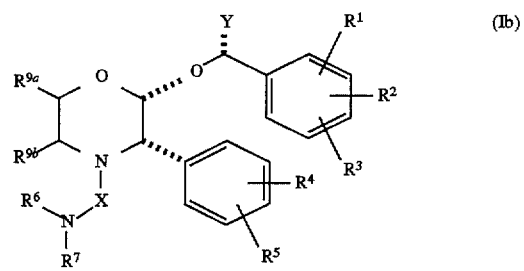

(Ib)

The present invention further provides pharmaceutical compositions comprising one or more compounds of formula (I) in association with a pharmaceutically acceptable carrier.

Preferably the compositions according to the invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (i), as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a premixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.5 µm, and have a pH in the range of 5.0 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic and chemotherapy-induced neuropathy, and postherpetic and other neuralgias; neuronal damage, such as cerebralischemic damage and cerebral edema in cerebrovascular disorders; small cell carcinomas such as small cell lung cancer; respiratory diseases, particularly those associated with excess mucus secretion such as chronic obstructive airways disease, bronchopneumonia, chronic bronchitis, asthma, and bronchospasm; airways diseases modulated by neurogenic inflammation; diseases characterised by neurogenic mucus secretion, such as cystic fibrosis; diseases associated with decreased glandular secretions, including lacrimation, such as Sjogren's syndrome, hyperlipoproteinemias IV and V, hemocromatosis, sarcoidosis, and amyloidosis; inflammatory diseases such as inflammatory bowel disease, psoriasis, fibrositis, ocular inflammation, osteoarthritis, rheumatoidarthritis, pruritis and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders including the withdrawal response produced by chronic treatment with, or abuse of, drugs such as benzodiazepines, opiates, cocaine, alcohol and nicotine; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed, post-operative, late phase or anticipatory emesis such as emesis induced by chemotherapy, radiation, toxins, vital or bacterial infections, pregnancy, vestibular disorders, motion, surgery, migraine, opioid analgesics, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, dental pain and that attributable to or associated with any of the foregoing conditions, especially the transmission of pain in migraine.

Hence, the compounds of the present invention may be of use in the treatment of physiological disorders associated with excessive stimulation of tachykinin receptors, especially neurokinin-1 receptors, and as neurokinin-1 antagonists for the control and/or treatment of any of the aforementioned clinical conditions in mammals, including humans.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed, post-operative, late phase or anticipatory emesis, such as emesis or nausea induced by chemotherapy, radiation, toxins, such as metabolic or microbial toxins, vital or bacterial infections, pregnancy, vestibular disorders, motion, mechanical stimulation, gastrointestinal obstruction, reduced gatrointestinal motility, visceral pain, psychological stress or disturbance, high altitude, weightlessness, opioid analgesics, intoxication, resulting for example from consumption of alcohol, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in "*Nausea and Vomiting: Recent Research and Clinical Advances*", Eds. J. Kuucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABAs receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126,375, 3,929, 768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5-R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a β2-adrenergic receptor antagonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene D4 antagonist such as a compound selected from those disclosed in European patent specification nos. 0 480 717 and 0 604 114 and in U.S. Pat. Nos. 4,859,692 and 5,270, 324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-HT$_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

According to one general process (A), the compounds of formula (I) in which the group —X-NR$^6$R$^7$ represents —CH$_2$CH$_2$NH$_2$, may be prepared from compounds of formula (II)

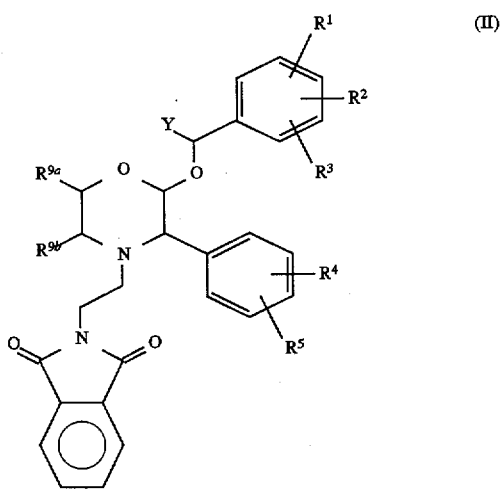

wherein R$^1$, R$^2$, R$^3$, R$^4$, R$^5$, R$^9$, R$^{9b}$ and Y are as defined in relation to formula (I) by reaction with hydrazine.

This reaction may be performed in conventional manner, for example in an organic solvent such as an alcohol, for example methanol, or a halogenated hydrocarbon, for example, dichloromethane, or a mixture thereof, conveniently at room temperature.

According to an alternative process (B), compounds of formula (I) wherein X is —CH$_2$CH$_2$—, may be prepared by reaction of a compound of formula (III)

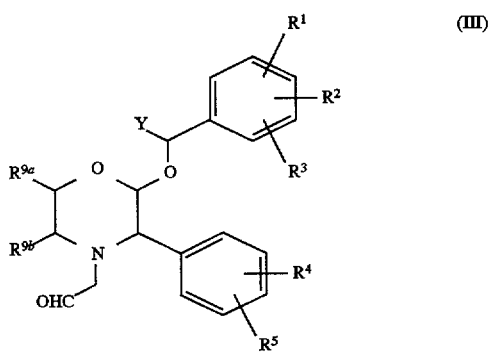

with an amine NHR$^6$R$^7$ under conventional conditions for reductive amination, in the presence of a suitable base, such as a hydride, e.g. sodium cyanoborohydride.

The reaction is conveniently effected in a suitable solvent such as a halogenated hydrocarbon, for example, dichloromethane, an alcohol, for example, methanol, or an amide, for example, dimethylformamide, or a mixture thereof.

According to a further process (C), compounds of formula (I) wherein X is —COCH$_2$—, may be prepared from intermediates of formula (IV)

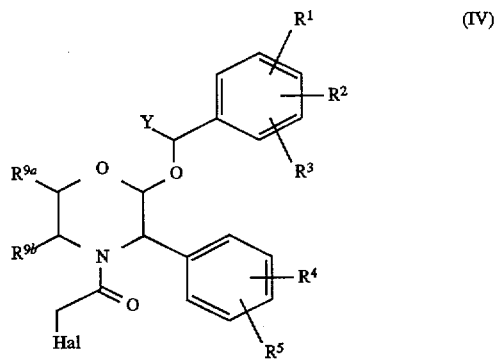

wherein Hal is a halogen atom such as chlorine, bromine or iodine, by reaction with an amine NHR$^6$R$^7$ in a conventional manner, for example in an organic solvent such as dimethylformamide in the presence of an acid acceptor such as potassium carbonate.

According to a further process (D), compounds of formula (I) may be prepared by the interconversion of a compound of formula (V):

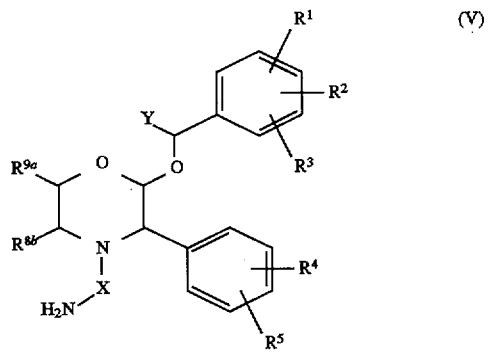

using alkyl halides of the formula R$^6$-Hal and R$^7$-Hal, or a suitable dihalide designed to form a saturated heterocyclic ring, wherein R$^6$ and R$^7$ are as previously defined, and Hal represents a halogen atom such as chlorine, bromine or iodine, in the presence of a base.

Suitable bases of use in the reaction include alkali metal carbonates, such as, for example, sodium bicarbonate.

The reaction is conveniently effected in a suitable organic solvent, such as, for example, acetonitrile, conveniently at room temperature.

Suitable dihalides for forming a saturated heterocyclic ring include, for example, Hal-(CH$_2$)$_4$-Hal (to give a pyrrolidino ring), Hal-(CH$_2$)$_2$O(CH$_2$)$_2$-Hal (to give a morpholino rang), or Hal-(CH$_2$)$_2$NR$^8$(CH$_2$)$_2$-Hal (to give a piperazino ring).

Alternatively, in another interconversion process for the preparation of a compound of formula (I) wherein R$^7$ is C(=NR$^c$)NR$^a$R$^b$, a compound of formula (V) may be reacted with a compound of formula (VI)

wherein Boc represents the protecting group t-butoxycarbonyl or a amine protecting group, followed by deprotection and, where necessary, by alkylation using a suitable alkyl halide such as methyl iodide in the presence of a base.

The reaction is conveniently effected in the presence of ethanol at reflux which has the effect of convening the group —NH-Boc into the group —NHCO$_2$CH$_2$CH$_3$.

Deprotection may be effected in a conventional manner using, for example, trifluoroacetic acid in dichloromethane.

Compounds of formula (I) may also be prepared from other compounds of formula (I) by reduction. For example, compounds of formula (I) wherein X represents C$_2$alkylene may be prepared from compounds of formula (I) wherein X represents C$_2$alkylene substituted by oxo by reduction, for example, using borane or lithium aluminum hydride. Other suitable interconversion procedures will be readily apparent to those skilled in the art.

Intermediates of formula (II) may be prepared from compounds of formula (VII)

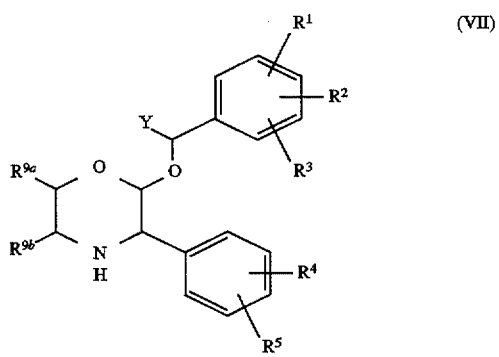

by reaction with a halogenated phthalimide compound of formula (VIII)

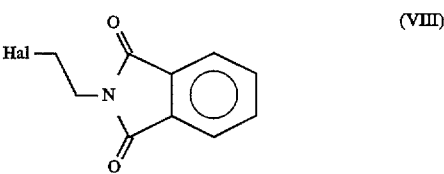

where Hal is as previously defined, in a conventional manner, for example in an organic solvent such as acetonitrile in the presence of an acid acceptor such as sodium hydrogencarbonate.

Intermediates of formula (III) may be prepared from intermediates of formula (VII) by reaction with, for example, methyl bromoacetate in the presence of a base such as cesium carbonate and a suitable organic solvent, such as dimethylformamide, followed by reduction using, for example, diisobutylaluminium hydride in a suitable solvent such as dichloromethane or toluene or a mixture thereof.

Similarly, intermediates of formula (IV) may be prepared from intermediates of formula (VII) by reaction with, for example, bromoacetyl bromide, in the presence of a suitable base.

Compounds of formula (VI) may be prepared as described in *J. Org. Chem*, 52, (1987), 1700.

The compounds of formula (VII) may be prepared as shown in the following scheme in which Ar$^1$ represents the R$^1$, R$^2$, R$^3$ substituted phenyl group; Ar$^2$ represents the R$^4$, R$^5$ substituted phenyl group and Ph represents phenyl:

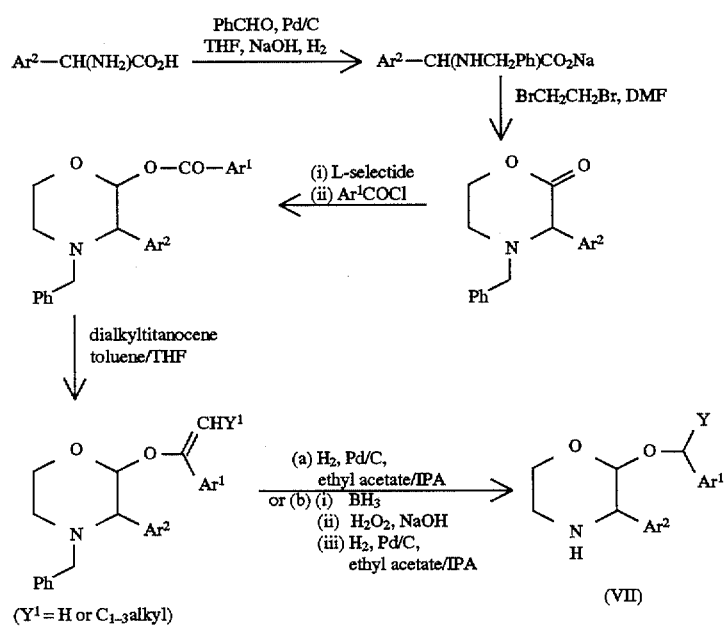

The following references describe methods which may be applied by the skilled worker to the chemical synthesis set forth above once the skilled worker has read the disclosure herein.

(i) D. A. Evans et al., *J. Am. Chem. Soc.*, 112, 4011 (1990).
(ii) Yanagisawa, I. et al., *J. Med. Chem.*, 27, 849 (1984).
(iii) Tebbe F. N. et al., *J. Am. Chem. Soc.*, 100, 3611 (1978).
(iv) Petasis, N. A. et al., *J. Am. Chem. Soc.*, 112, 6532 (1990).
(v) Takai, K. et al., *J. Org. Chem.*, 52, 4412 (1987).

The Examples disclosed herein produce predominently the preferred isomers. The unfavoured isomers are also produced on minor components. If desired they may be isolated and employed to prepare the various stereoisomers in conventional manner, for example chromatography using an appropriate chiral column. However, the skilled worker will appreciate that although the Examples have been optimized to the production of the preferred isomers, variation in solvent, reagents, chromatography etc can be readily employed to yield the other isomers.

L-Selectride is lithium tri-sec-butylborohydride.

Where they are not commercially available, the intermediates above may be prepared by the procedures described in the accompanying Examples or by alternative procedures which will be readily apparent to one skilled in the art.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the NK1 receptor of less than 100 nM.

The compounds of this invention may be formulated as specifically illustrated at pages 35 to 36 or International Patent Specification No. WO 93/01165.

The following Examples illustrate the preparation of compounds according to the present invention:

DESCRIPTION 1

(S)-(4-Fluorophenyl) glycine
Via Chiral Synthesis:
Step A: 3-(4-Fluorophenyl)acetyl-4-(S)-benzyl-2-oxazolidinone An oven-dried, 1 L 3-necked flask, equipped with a septum, nitrogen inlet, thermometer, and a magnetic stirring bar, was flushed with nitrogen and charged with a solution of 4-fluorophenylacetic acid (5.09 g; 33.0 mmol) in anhydrous ether (100 ml). The solution was cooled to −10° C. and treated with triethylamine (5.60 ml; 40.0 mmol) followed by trimethylacetyl chloride(4.30 ml; 35.0 mmol). A white precipitate formed immediately. The resulting mixture was stirred at −10° C. for 40 minutes, then cooled to −78° C.

An oven-dried, 250 ml round bottom flask, equipped with a septum and a magnetic stirring bar, was flushed with nitrogen and charged with a solution of 4-(S)-benzyl-2-oxazolidinone (5.31 g; 30.0 mmol) in dry THF (40 ml). The solution was stirred in a dry ice/acetone bath for 10 minutes, then n-butyllithium solution in hexanes (18.8 ml; 1.6M) was slowly added. After 10 minutes, the lithiated oxazolidinone solution was added, via cannula, to the above mixture in the 3-necked flask. The cooling bath was removed from the resulting mixture and the temperature was allowed to rise to 0° C. The reaction was quenched with saturated aqueous ammonium chloride solution (100 ml), transferred to a 1 l flask, and the ether and THF were removed in vacuo. The concentrated mixture was partitioned between methylene chloride (300 ml) and water (50 ml) and the layers were separated. The organic layer was washed with 2N aqueous hydrochloric acid solution (100 ml), saturated aqueous sodium bicarbonate solution (300 ml), dried over magnesium sulfate and concentrated in vacuo. Flash chromatography on silica gel (400 g) using 3:2 v/v hexanes/ether as the eluant afforded an oil (8.95 g) that slowly solidified on standing. Recrystallisation from 10:1 hexanes/ether afforded the title compound (7.89 g; 83%) as a white solid: mp 64°–66° C. MS (FAB): m/z 314 ($M^+$+H, 100%), 177 (M-$ArCH_2CO$+H, 85%). $^1$H NMR (400 MHz, $CDCl_3$) δ 2.76 (1H, dd, J=13.2, 9.2 Hz), 3.26 (dd, J=13.2, 3.2 Hz), 4.16–4.34 (4H, m), 4.65 (1H, m), 7.02–7.33 (9H, m). Anal. Calcd for $C_{18}H_{16}FNO_3$; C, 69.00; H, 5.15; N, 4.47; F, 6.06; Found: C, 68.86; H, 5.14; N, 4.48; F, 6.08.

Step B: 3-((S)-Azido-(4-fluorophenyl))acetyl-4-(S)-benzyl-2-oxazolidinone

An oven-dried, 1l 3-necked flask, equipped with a septum, nitrogen inlet, thermometer, and a magnetic stirring bar, was flushed with nitrogen and charged with a solution of 1M potassium bis(trimethylsilyl)amide solution (58.0 ml) in toluene and THF (85 ml) and was cooled to −78° C. An oven-dried 250 ml round-bottomed flask, equipped with a septum and a magnetic stirring bar, was flushed with nitrogen and charged with a solution of 3-(4-fluorophenyl)acetyl-4-(S)-benzyl-2-oxazolidinone (7.20 g; 23.0 mmol) (from Step A) in THF (40 ml). The acyl oxazolidinone solution was stirred in a dry ice/acetone bath for 10 minutes, then transferred, via cannula, to the potassium bis(trimethylsilyl) amide solution at such a rate that the internal temperature of the mixture was maintained below −70° C. The acyl oxazolidinone flask was rinsed with THF (15 ml) and the rinse was added, via cannula, to the reaction mixture and the resulting mixture was stirred at −78° C. for 30 minutes. An oven-dried, 250 ml round-bottomed flask, equipped with a septum and a magnetic stirring bar, was flushed with nitrogen and charged with a solution of 2,4,6-triisopropylphenylsulfonyl azide (10.89 g; 35.0 mmol) in THF (40 ml). The azide solution was stirred in a dry ice/acetone bath for 10 minutes, then transferred, via cannula, to the reaction mixture at such a rate that the internal temperature of the mixture was maintained below −70° C. After 2 minutes, the reaction was quenched with 6.0 ml of glacial acetic acid, the cooling bath was removed and the mixture was stirred at room temperature for 18 hours. The quenched reaction mixture was partitioned between ethyl acetate (300 ml) and 50% saturated aqueous sodium bicarbonate solution (300 ml). The organic layer was separated, dried over magnesium sulfate, and concentrated in vacuo. Flash chromatography on silica gel (500 g) using 2:1 v/v, then 1:1 v/v hexanes/methylene chloride as the eluant afforded the title compound (5.45 g; 67%) as an oil. IR Spectrum (neat, $cm^{-1}$): 2104, 1781, 1702. $^1$H NMR (400 MHz, $CDCl_3$) δ 2.86 (1H, dd, J=13.2, 9.6 Hz), 3.40 (1H, dd, J=13.2, 3.2 Hz), 4.09–4.19 (2H, m), 4.62–4.68 (1H, m), 6.14 (1H, s), 7.07–7.47 (9H, m). Anal. Calcd. for $C_{18}H_{15}FN_4O_3$; C 61.01; H, 4.27; N, 15.81; F, 5.36; Found: C, 60.99; H, 4.19; N, 15.80; F, 5.34.

Step C: (S)-Azido-(4-fluorophenyl)acetic acid

A solution of 3-((S)-azido-(4-fluorophenyl))-acetyl-4-(S)-benzyl-2-oxazolidinone (5.40 g; 15.2 mmol) (from Step B)

in 3:1 v/v THF/water (200 ml) was stirred in an ice bath for 10 minutes. Lithium hydroxide monohydrate (1.28 g; 30.4 mmol) was added in one portion and the resulting mixture was stirred cold for 30 minutes. The reaction mixture was partitioned between methylene chloride (100 ml) and 25% saturated aqueous sodium bicarbonate solution (100 ml) and the layers were separated. The aqueous layer was washed with methylene chloride (2×100 ml) and acidified to pH 2 with 2N aqueous hydrochloric acid solution. The resulting mixture was extracted with ethyl acetate (2×100ml); the extracts were combined, washed with saturated aqueous sodium chloride solution (50 ml), dried over magnesium sulfate, and concentrated in vacuo to afford the title compound (2.30 g; 77%) as an oil that was used in the following step without further purification. IR Spectrum (neat, cm$^{-1}$): 2111, 1724. $^1$H NMR (400 MHz, CDCl$_3$) δ 5.06 (1H, s), 7.08–7.45 (4H, m), 8.75 (1H, br s).

Step D: (S)-(4-Fluorophenyl)glycine

A mixture of (S)-azido-(4-fluorophenyl)acetic acid (2.30 g; 11.8 mmol) (from Step C), 10% palladium on carbon catalyst (2.50 mg) and 3:1 v/v water/acetic acid (160 ml) was stirred under an atmosphere of hydrogen for 18 hours. The reaction mixture was filtered through Celite and the flask and filter cake were rinsed well with ~1l of 3:1 v/v water/acetic acid. The filtrate was concentrated in vacuo to about 50 ml of volume. Toluene (300 ml) was added and the mixture concentrated to afford a solid. The solid was suspended in 1:1 v/v methanol/ether, filtered and dried to afford the title compound (1.99 g; 100%). $^1$H NMR (400 MHz, D$_2$O+NaOD) δ 3.97 (1H, s), 6.77 (2H, app t, J=8.8 Hz), 7.01 (2H, app t, J=5.6 Hz).

Via Resolution:

Step A' (4-Fluorophenyl)acetyl chloride

A solution of 4-(fluorophenyl)acetic acid (150 g; 0.974 mol) and N,N-dimethylformamide (1 ml) in toluene (500 ml) at 40° C. was treated with thionyl chloride (20 ml) and heated to 40° C. An additional thionyl chloride (61.2 ml) was added dropwise over 1.5 hours. After the addition, the solution was heated at 50° C. for 1 hour, the solvent was removed in vacuo and the residual oil was distilled at reduced pressure (1.5 mmHg) to afford the title compound (150.4 g; 89.5%), bp=68°–70° C.

Step B': Methyl 2-bromo-3-(4-fluorophenyl)acetate

A mixture of 4-(fluorophenyl)acetyl chloride (150.4 g; 0.872 mol) (from Step A') and bromine (174.5 g; 1.09 mol) was irradiated at 40°–50° C. with a quartz lamp for 5 hours. The reaction mixture was added dropwise to 400 ml of methanol and the solution was stirred for 16 hours. The solvent was removed in vacuo and the residual oil was distilled at reduced pressure (1.5 mm Hg) to afford the title compound (198.5 g; 92%). bp=106°–110° C.

Step C': Methyl(±-(4-fluorophenyl)glycine

A solution of methyl 2-bromo-2-(4-fluorophenyl)acetate (24.7 g; 0.1 mol) (from Step B') and benzyl triethylammonium chloride (2.28 g; 0.01 mmol) in methanol (25 ml) was treated with sodium azide (6.8 g; 0.105 mmol) and the resulting mixture was stirred for 20 hours at room temperature. The reaction mixture was filtered; the filtrate was diluted with 50 ml of methanol and hydrogenated in the presence of 0.5 g of 10% Pd/C at 50 psi for 1 hour. The solution was filtered and the solvent removed in vacuo. The residue was partitioned between 10% aqueous sodium carbonate solution and ethyl acetate. The organic phase was washed with water, saturated aqueous sodium chloride solution dried over magnesium sulfate and concentrated in vacuo to afford 9.8 g of the title compound as an oil.

Step D': Methyl(S)-(4-flurophenyl)glycinamate

A solution of 58.4 g of methyl (±) 4-(fluorophenyl) glycinate (from Step C') in 110 ml of 7:1 v/v ethanol/water was mixed with a solution of O,O'-(+)-dibenzoyltartaric acid ((+)-DBT) (28.6 g, 0.0799 mol) in 110 ml of 7:1 v/v ethanol:water and the resulting solution was allowed to age at room temperature. Ethyl acetate (220 ml) was added after crystallisation was complete and the resulting mixture was cooled to −20° C. and filtered to afford 32.4 g of methyl (S)-(4-fluorophenyl)glycinate, (+)-DBT salt (ee=93.2%). The mother liquors were concentrated in vacuo and the free base was liberated by partitioning between ethyl acetate and aqueous sodium carbonate solution. A solution of free base, so obtained, in 110 ml of 7:1 v/v ethanol/water was mixed with a solution of O,O'-(−)-dibenzoyltartaric acid ((−)-DBT) (28.6 g, 0.0799 mol) in 110 ml of 7:1 v/v ethanol:water and the resulting solution was allowed to age at room temperature. Ethyl acetate (220 ml) was added after crystallisation was complete and the resulting mixture was cooled to −20° C. and filtered to afford 47.0 g of methyl (R)-(4-fluorophenyl)glycinate, (−)-DBT salt (ee=75.8%). Recycling of the mother liquors and addition of (−)-DBT gave a second crop of 7.4 g of (S)-(4-fluorophenyl)glycinate, (+)-DBT salt (ee=96.4%). The two crops of the (S)-amino ester (39.8 g) were combined in 200 ml of 7:1 v/v ethanol/water, heated for 30 minutes and cooled to room temperature. Addition of ethyl acetate, cooling, and filtration afforded 31.7 g of (S)-(4-fluorophenyl)glycinate, (+)-DBT salt (ee>98%). Enantiomeric excess was determined by chiral HPLC (Crownpak CR(+) 5% MeOH in aq HClO4 pH2 1.5 ml/min 40° C. 200 nm).

A mixture of 17.5 g of (S)-(4-fluorophenyl)glycinate, (+)-DBT salt and 32 ml of 5.5 N HCl (32 ml) was heated at reflux for 1.5 hours. The reaction mixture was concentrated in vacuo and the residue was dissolved in 40 ml of water. The aqueous solution was washed with ethyl acetate (3×30 ml) and the layers were separated. The pH of the aqueous layer was adjusted to 7 using ammonium hydroxide and the precipitated solid was filtered to afford 7.4 g of the title compound (ee=98.8%).

DESCRIPTION 2

4-Benzyl-3-(S)-(4-fluorophenyl-2-morpholinone

Step A: N-Benzyl-(S)-(4-fluorophenyl)glycine

A solution of (S)-(4-fluorophenyl)-glycine (1.87 g; 11.05 mmol) (from Description 1) and benzaldehyde (1.12 ml; 11.1 mmol) in 1N aqueous sodium hydroxide solution (11.1 ml) and methanol (11 ml) at 0° C. was treated with sodium borohydride (165 mg; 4.4 mmol). The cooling bath was removed and the resulting mixture was stirred at room temperature for 30 minutes. Second portions of benzaldehyde (1.12 ml; 11.1 mmol) and sodium borohydride (165 mg; 4.4 mmol) were added to the reaction mixture and stirring was continued for 1.5 hours. The reaction mixture was partitioned between 100 ml of ether and 50 ml of water and the layers were separated. The aqueous layer was separated and filtered to remove a small amount of insoluble material. The filtrate was acidified to pH 5 with 2N aqueous hydrochloric acid solution and the solid that had precipitated was filtered, rinsed well with water, then ether, and dried to afford 1.95 g of the title compound. $^1$H NMR (400 MHz, D$_2$O+NaOD) δ 3.33 (2H, AB q, J=8.4 Hz), 3.85 (1H, s), 6.79–7.16 (4H, m).

Step B: 4-Benzyl-3-(S)-(4-fluorophenyl)-2-morpholinone

A mixture of 1.95 g (7.5 mmol) of N-benzyl (S)-(4-fluorophenyl)glycine, 3.90 ml (22.5 mmol) of N,N-diisopropyl-ethylamine, 6.50 ml (75.0 mmol) of 1,2-dibromoethane and 40 ml of N,N-dimethylformamide was stirred at 100° C. for 20 hours (dissolution of all solids occurred on warming). The reaction mixture was cooled and concentrated in vacuo. The residue was partitioned between 250 ml of ether and 100 ml of 0.5N potassium hydrogen sulfate solution and the layers were separated. The organic layer was washed with 100 ml of saturated aqueous sodium bicarbonate solution, 3×150 ml of water, dried over magnesium sulfate, and concentrated in vacuo. Flash chromatography on 125 g of silica gel using 3:1 v/v hexanes/ether as the eluant afforded 1.58 g (74%) of the title compound as an oil. $^1$H NMR (400 MHz, CDCl$_3$) δ 2.65 (1H, dt, J=3.2, 12.8 Hz), 3.00 (1H, dt, J=12.8, 2.8 Hz), 3.16 (1H, d, J=13.6 Hz), 3.76 (1H, d, J=13.6 Hz), 4.24 (1H, s), 4.37 (1H, dt, J=13.2, 3.2 Hz), 4.54 (1H, dt, J=2.8, 13.2 Hz), 7.07–7.56 (9H, m).

DESCRIPTION 3

4-Benzyl-2-(R)-(3,5-bis(trifluoromethyl)benzoyloxy)-3-(S)-(4-fluorophenyl)morpholine A solution of 2.67 g (10.0 mmol) of 4-benzyl-3-(S)-(4-fluorophenyl)-2-morpholinone (Description 2) in 40 ml of dry THF was cooled to −78° C. The cold solution was treated with 12.5 ml of 1.0M L-Selectride® solution in THF, maintaining the internal reaction temperature below −70° C. The resulting solution was stirred cold for 45 minutes and the reaction was charged with 3.60 ml (20.0 mmol) of 3,5-bis(trifluoromethyl)benzoyl chloride. The resulting yellow mixture was stirred cold for 30 minutes and the reaction was quenched with 5 0ml of saturated aqueous sodium bicarbonate solution. The quenched mixture was partitioned between 300 ml of ether and 50 ml of water and the layers were separated. The organic layer was dried over magnesium sulfate. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid. $^1$H NMR (200 MHz, CDCl$_3$) δ 2.50 (1H, dr, J=3.4, 12.0 Hz), 2.97 (1H, app d, J=12.0 Hz), 2.99 (1H, d, J=13.6 Hz), 3.72–3.79 (1H, m), 3.82 (1H, d, J=2.6 Hz), 4.00 (1H, d, J=13.6 Hz), 4.20 (dr, J=2.4, 11.6 Hz), 6.22 (1H, d, J=2.6 Hz), 7.22–7.37 (7H, m), 7.57 (2H, app d, J=6.8 Hz), 8.07 (1H, s), 8.47 (2H, s). MS (FAB) m/z 528 (M+H, 25%), 270 (100%). Anal. Calcd for C$_{26}$H$_{20}$F$_7$NO$_3$; C, 59.21; H, 3.82; N, 2.66; F, 25.21. Found: C, 59.06; H, 4.05; N, 2.50; F, 25.18.

DESCRIPTION 4

4-Benzyl-2-(R)-(1-(3,5-bis(trifluoromethyl)phenyl)ethenyloxy)-3-(S)-(4-fluorophenyl)morpholine
Step A: Dimethyl titanocene A solution of 2.49 g (10.0 mmol) of titanocene dichloride in 50 ml of ether in the dark at 0° C. was treated with 17.5 ml of 1.4M methyllithium solution in ether maintaining the internal temperature below 5° C. The resulting yellow/orange mixture was stirred at room temperature for 30 minutes and the reaction was quenched by slowly adding 25 g of ice. The quenched reaction mixture was diluted with 50 ml of ether and 25 ml of water and the layers were separated. The organic layer was dried over magnesium sulfate and concentrated in vacuo to afford 2.03 g (98%) of the title compound as a light-sensitive solid. The dimethyl titanocene could be stored as a solution in toluene at 0° C. for at least 2 weeks without apparent chemical degradation. $^1$H NME (200 MHz, CDCl$_3$) δ −0.15 (6H, s), 6.06 (10H, s).

Step B: 4-Benzyl-2-(R)trifluoromethyl)phenyl)ethenyloxy)-3-4-fluorophenyl)morpholine A solution of the compound of Description 3 (2.50 g, 4.9 mmol) and 2.50 g (12.0 mmol) of dimethyl titanocene (from Step A) in 35 ml of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. An analytical sample was obtained via recrystallisation from isopropanol: $^1$H NMR (400 MHz, CDCl$_3$) δ2.42 (1H, dr, J=3.6, 12.0 Hz), 2.90 (1H, app d, J=12.0 Hz), 2.91 (1H, d, J=13.6 Hz), 3.62–3.66 (1H, m), 3.72 (1H, d, J=2.6 Hz), 3.94 (1H, d, J=13.6 Hz), 4.09 (1H, dt, J=2.4, 12.0 Hz), 4.75 (1H, d, J=3.2 Hz), 4.82 (1H, d, J=3.2 Hz), 5.32 (1H, d, J=2.6 Hz), 7.09 (2H, t, J=8.8 Hz), 7.24–7.33 (5H, m), 7.58–7.62 (2H, m), 7.80 (1H, s), 7.90 (2H, s); MS (FAB) 526 (M+H, 75%), 270 (100%). Anal. Calcd for C$_{27}$H$_{22}$F$_7$NO$_2$: C, 61.72; H, 4.22; N, 2.67; F, 25.31. Found: C, 61.79; H, 4.10; N, 2.65; F, 25.27.

DESCRIPTION 5

2-(R)-(1-R)-(3,5-Bis(trifluoromethyl)phenyl)ethoxy)-3-(S)-4-fluorophenyl)morpholine The compound of Description 4 (4.0 g) was dissolved in ethyl acetate (50 ml) and isopropanol (16 ml). To this solution was added palladium on charcoal (1.5 g) and the mixture was hydrogenated at 40 psi for 36h. The catalyst was removed by filtration through Celite and the solvents were removed in vacuo. The residue was purified by flash chromatography on silica using 100% ethyl acetate and then 1–10% methanol in ethyl acetate. This afforded isomer A 500 mg (15%) and isomer B 2.6 g (80%) as clear oils—isomer B crystallized on standing. For the title compound: $^1$H NMR (400 MHz, CDCl$_3$) δ 1.16 (3H, d, J=6.8 MHz), 1.80 (1H, br s), 3.13 (1H, dd, J=3.2, 12.4 Hz), 3.23 (1H, dt, J=3.6, 12.4 Hz), 3.63 (1H, dd, J=2.4, 11.2 Hz), 4.01 (1H, d, J=2.4 Hz), 4.13 (1H, d, J=3.2, 12.0Hz), 4.42 (1H, d, J=2.4 Hz), 4.19 (1H, q, J=6.8 Hz), 7.04–7.09 (2H, m), 7.27–7.40 (4H, m), 7.73 (1H, s); MS (FAB) 438 (M+H, 75%), 180 (100%).

DESCRIPTION 6

4-Benzyl-3-(S)-phenyl-2-morpholinone
Step A: N-Benzyl-(S)-phenylglycine

A solution of 1.51 g (10.0 mmol) of (S)-phenylglycine in 5 ml of 2N aqueous sodium hydroxide solution was treated with 1.0 ml (10.0 mmol) of benzaldehyde and stirred at room temperature for 20 minutes. The solution was diluted with 5 ml of methanol, cooled to 0° C., and carefully treated with 200 mg (5.3 mmol) of sodium borohydride. The cooling bath was removed and the reaction mixture was stirred at room temperature for 1.5 hours. The reaction was diluted with 20 ml of water and extracted with 2×25 ml of methylene chloride. The aqueous layer was acidified with concentrated hydrochloric acid to pH 6 and the solid that precipitated was filtered, washed with 50 ml of water, 50 ml of 1:1 v/v methanol/ethyl ether and 50 ml of ether, and dried to afford 1.83 g (76%) of product, mp 230°–232° C. Anal. Calcd for C$_{15}$H$_{15}$NO$_2$: C, 74.66; H, 6.27; N, 5.81. Found: C, 74.17; H, 6.19; N, 5.86.

Step B: 4-Benzyl-3-(S)-phenyl-2-morpholinone

A mixture of 4.00 g (16.6 mmol) of N-benzyl-(S)-phenylglycine (from Step A) 5.00 g (36.0 mmol) of potassium carbonate, 10.0 ml of 1,2-dibromoethane and 25 ml of N,N-dimethylformamide was stirred at 100° C. for 20 hours. The mixture was cooled and partitioned between 200 ml of ethyl ether and 100 ml of water. The layers were separated and the organic layer was washed with 3×50 ml of water, dried over magnesium sulfate and concentrated in vacuo. The residue was purified by flash chromatography on 125 g of silica gel eluting with 9:1 v/v, then 4:1 hexanes/ethyl ether to afford 2.41 g (54%) of the product as a solid, mp 98°–100° C. $^1$H NMR (250 MHz, CDC$_3$) δ 2.54–2.68 (1H, m), 2.96 (1H, dt, J=12.8, 2.8 Hz), 3.14 (1H, d, J=13.3 Hz), 3.75 (1H, d, J=13.3 Hz), 4.23 (1H, s), 4.29–4.37 (1H, m), 4.53 (dr, J=3.2, 11.0 Hz), 7.20–7.56 (10H, m). MS (FAB): m/z 268 (M+H; 100%). Anal. Calcd for C$_{17}$H$_{17}$NO$_2$: C, 76.38; H, 6.41; N, 5.24. Found: C, 76.06; H, 6.40; N, 5.78.

DESCRIPTION 7

2-(S)-(3,5-Bis(trifluoromethyl)benzyloxy)-3-(S)-phenylmorpholine

Step A: 3,5-Bis(trifluoromethyl)benzyl alcohol, trifluoromethanesulfonate ester

A solution of 3,5-bis(trifluoromethyl)benzyl alcohol (1.00 g) and 2,6-di-tert-butyl-4-methylpyridine (1.05 g) in dry carbon tetrachloride (45 ml) under a nitrogen atmosphere was treated with trifluoromethanesulfonate anhydride (0.74 ml) at room temperature. A white precipitate formed shortly after the addition of the anhydride. After 90 min, the slurry was filtered under nitrogen with a Schlenk filter, and the filtrate was concentrated in vacuo. The residue, which was a two-phase oil, was dissolved under nitrogen in 10 ml of dry toluene. The resulting clear solution was used immediately in Step B below.

Step B 4-Benzyl-2-(S)-(3,5-bis(trifluoromethyl)benzyloxy)-3-(S)-phenylmorpholine A solution of the compound of Description 6 (0.5 g) in dry THF (10 ml) was cooled to −75° C. under nitrogen and was treated drop wise with 2.06 ml of a 1M solution of lithium tri(sec-butyl)-borohydride (L-Selectride®) in THF. After stirring the solution at −75° C. for 30 min, a solution of 3,5-bis(trifluoromethyl)benzyl alcohol, trifluoromethanesulfonate ester in toluene was added by cannula so that the internal temperature was maintained below −60° C. The resulting solution was stirred at −75° C. for 1 hr and then between −38° C. and −50° C. for 2 hr. The solution was then poured into a mixture of 25 ml of ethyl acetate and 20 ml of saturated aqueous sodium bicarbonate, and the layers were separated. The aqueous phase was extracted with 2×30 ml of ethyl acetate, the combined organic layers were dried over sodium sulfate, the mixture was filtered and the filtrate concentrated in vacuo. The residue was purified by flash chromatography on 130 g of silica eluting with 2 L of 100:5 hexanes:ethyl acetate to give 0.68 g (73%) of an oil, which by $^1$H is a 20:1 mixture of cis-trans morpholines. $^1$H NMR (400 MHz, CDCl$_3$) δ major (cis) isomer: 2.37 (1H, td, J=12, 3.6 Hz), 2.86 (2H, app t, J=13 Hz), 3.57 (1H, d, J=2.6 Hz), 3.63 (1H, dq, J=11.3, 1.6 Hz), 3.89 (1H, d, J=13:3 Hz), 4.12 (1H, td, J=11.6, 2.4 Hz), 4.40 (1H, d, J=13.6 Hz), 4.69 (1H, d, J=2.9 Hz), 4.77 (d, J=13.6 Hz), 7.2–7.4 (5H, m), 7.43 (2H, s), 7.55 (2H, br d), 7.69 (1H, s).

Step C: 2-(S)-(3,5-Bis(trifluoromethyl)benzyloxy)-3-(S)-phenylmorpholine

A mixture of 0.68 g of 4-benzyl-2-(S)-(3,5-bis (trifluoromethyl)benzyloxy)-3-(S)-phenylmorpholine and 280 mg of 10% Pd/C in 36 ml of 97:3 ethanol:water was stirred under one atmosphere of hydrogen for 15 hr. The mixture was filtered through Celite, the filter cake was washed generously with ethanol, and the filtrate was concentrated in vacuo. The residue was purified by flash chromatography on 68 g of silica eluting with 1 L of 33:67 hexanes:diethyl ether, then 1 L of 25:75 hexanes:diethyl ether to give 0.443 g (80%) of an oil, which by $^1$H NMR was pure cis morpholine. $^1$H NMR (400 MHz, CDCl$_3$) δ 1.8 (1H, br s), 3.10 (1H, dd, J=12.5, 2.9 Hz), 3.24 (1H, td, J=12.2, 3.6 Hz), 3.62 (1H, dd, J=11.3, 2.5 Hz), 4.04 (1H, td, J=11.7, 3 Hz), 4.11 (1H, d, J=2.4Hz), 4.49 (1H, d, J=13.5 Hz), 4.74 (1H, d, J=2.5 Hz), 4.80 (1H, d, J=13.3 Hz), 7.25–7.40 (5H, m), 7.40 (2H, s), 7.68 (1H, s). Anal. Calcd. For C$_{19}$H$_{17}$F$_6$NO$_2$: C, 56.30; H, 4.23; N, 3.46; F, 28.12. Found: C, 56.20; H, 4.29; N, 3.34; F, 27.94.

DESCRIPTION 8

4-Benzyl-2-(R)-(3,5-bis(trifluoromethyl)benzoyloxy)-3-(S)-phenylmorpholine

A solution of 2.67 g (10.0 mmol) of the compound of Description 6 in 40 ml of dry THF was cooled to −78° C. The cold solution was treated with 12.5 ml of 1.0M L-Selectride® solution in THF, maintaining the internal reaction temperature below −70° C. The resulting solution was stirred cold for 45 minutes and the reaction was charged with 3.60 ml (20.0 mmol) of 3,5-bis(trifluoromethyl)benzoyl chloride. The resulting yellow mixture was stirred cold for 30 minutes and the reaction was quenched with 50 ml of saturated aqueous sodium bicarbonate solution. The quenched mixture was partitioned between 300 ml of ether and 50 ml of water and the layers were separated. The organic layer was dried over magnesium sulfate. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid. $^1$H NMR (200 MHz ppm, CDCl$_3$) δ 2.50 (1H, dt, J=3.4, 12.0), 2.97 (1H, app d, J=12.0), 2.99 (1H, d, J=13.6), 3.72–3.79 (1H, m), 3.82 (1H, d, J=2.6), 4.00 (1H, d, J=13.6), 4.20 (dr, J=2.4, 11.6), 6.22 (1H, d, J=2.6), 7.22–7.37 (7H, m), 7.57 (2H, appd, J=6.8), 8.07 (1H, s), 8.47 (2H, s). Anal. Calcd for C$_{26}$H$_{21}$F$_6$NO$_3$: C, 61.29; H, 4.16; N, 2.75; F, 22.38. Found: C, 61.18; H, 4.14; N, 2.70; F, 22.13.

DESCRIPTION 9

4-Benzyl-2-(R)-(1-(3,5-bis(trifluoromethyl)phenyl) ethenyloxy)-3-(S)-phenylmorpholine A solution of 2.50 g (4.9 mmol) of the compound of Description 8 and 2.50 g (12.0 mmol) of dimethyl titanocene (Description 4a), in 35 ml of 1:1 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71g (69%) of the title compound as a solid. $^1$H NMR (400 MHz, CDCl$_3$) δ 2.42 (1H, dt, J=3.6, 12.0), 2.89 (app d, J=11.6), 2.92 (1H, d, J=13.6), 3.61–3.66 (1H, m), 3.73 (1H, d, J=2.8), 4.00 (1H, d, J=13.6), 4.09 (1H, dt, J=2.4, 11.6), 4.75 (1H, d, J=2.8), (1H, d, J=2.8), 5.36 (1H, d, J=2.4), 7.23–7.41 (7H, m), 7.63 (1H, app d, J=7.2), 7.79 (1H, s), 7.91 (2H, s). MS (FAB) m/z 508 (M+1, 25%). Anal. Calcd. for C$_{27}$H$_{23}$F$_6$NO$_2$: C, 63.90; H, 4.57; N, 2.76; F, 22.46. Found: C, 63.71; H, 4.53; N, 2.68; F, 22.66.

DESCRIPTION 10

2-(R)-(1-(S)-(3,5-Bis(trifluoromethyl)phenyl)ethoxy)-3-(S)-phenylmorpholine

A mixture of the compound of Description 9 (1.5 g) and 10% palladium on carbon catalyst (750 mg) in a mixture of isopropanol/ethyl acetate (25 ml, 3:2 v/v) was stirred under an atmosphere of hydrogen for 48h. The catalyst was removed by filtration through celite and the reaction flask and filter pad were rinsed with ethyl acetate (500 ml). The filtrate was concentrated in vacuo, flash chromatography afforded epimer A (106 mg) and epimer B (899 mg) as clear oils. The title compound, epimer B had the following analysis: $^1$H NMR (CDCl$_3$, 400 MHz) δ 1.46 (3H, d, J=6.8Hz), 1.92 (1H, brs), 3.13 (1H, dd, J=3.0, 12.6 Hz), 3.24 (1H, dr, J=3.6, 12.6Hz), 3.62 (1H, dd, J=3.6, 11.2 Hz), 4.04 (1H, d, J=2.4 Hz), 4.14 (1H, dt, J=3.0, 11.2 Hz), 4.48 (1H, d, J=2.4 Hz), 4.90 (1H, q, J=6.8 Hz), 7.21–7.32 (7H, m), 7.64 (1H, s MS (CI$^+$) m/z 420 (M$^+$+I, 20%), 178 (100%). Anal. Calcd. for C$_{20}$H$_{19}$F$_6$NO$_2$; C, 57.28; H, 4.57; N, 3.34; F, 27.18. Found: C, 57.41; H, 4.61; N, 3.29; F, 27.23.

DESCRIPTION 11

3-(S)-Phenyl-2-(R)-(1-(R)-(3-(trifluoromethyl)phenyl) ethoxy)morpholine

The title compound was prepared from the compound of Description 6 using procedures analogous to those in Descriptions 8–10. $^1$H NMR (400 MHz, CDCl$_3$) δ 1.39 (3H, d, J=6.6 Hz), 1.93 (1H, brs), 3.10 (1H, dd, J=12.7, 3.0 Hz), 3.20 (1H, dr, J=12.4, 3.6 Hz), 3.58 (1H, ddd, J=1.1, 3.8, 11.2 Hz), 4.00 (1H, d, J=2.4 Hz), 4.12 (1H, dt, J =3.0, 11.2 Hz), 4.44 (1H, d, J=2.4 Hz), 4.79 (1H, q, J=6.6 Hz), 6.72 (1H, d, J=7.7 Hz), 7.01 (1H; s), 7.09 (1H, t, J=7.7 Hz), 7.18–7.25 (2H, m), 7.25–7.3 (3H, m), 7.34 (1H, d, J=7.7 Hz). Anal. Calcd. For C$_{19}$H$_{19}$F$_3$NO$_2$: C, 65.14; H, 5.47; N, 4.00; F, 16.27. Found: C, 64.89; H, 5.73; N, 3.83; F, 15.95[[]jf44a

DESCRIPTION 12

2-(R)-(1-(R)-(3-Fluoro-5-(trifluoromethyl)phenyl) ethoxy)-3-(S)-phenylmorpholine The title compound was prepared in 44% yield from the compound of Description 6 following procedures analogous to Descriptions 8–10. $^1$H NMR (400 MHz, CDCl$_3$) δ 1.38 (3H, d, J=6.6 Hz), 1.90 (1H, brs), 3.17 (1H, dd, J=3.0, 12.7 Hz), 3.18 (1H, dr, J=12.7, 3.6 Hz), 3.58 (1H, ddd, J=1.1, 3.8, 11.2 Hz), 4.02 (1H, d, J=2.3 Hz), 4.11 (1H, dt, J=3.0, 11.2 Hz), 4.44 (1H, d, J=2.3 Hz), 4.78 (1H, q, J=6.6 Hz), 6.29 (1H, d, J =9.2Hz), 6.85 (1H, s), 7.03 (1H, d, J=8.4 Hz), 7.18–7.26 (2H, m), 7.26–7.3 (3H, m). Anal. Calcd. For C$_{19}$H$_{18}$F$_4$NO$_2$: C, 61.95; H, 4.93; N, 3.80; F, 20.63. Found: C, 61.78; H, 5.14; N, 3.71; F, 20.35%.

EXAMPLE 1

4-(2.-Aminoethyl)-2-(R)-(1 -(R)-(3,5-bis(trifluoromethyl) phenyl)ethoxy)-3-(S)-(4-fluorophenyl)morpholine
(a) 2-(R)-(1-(R)-(3,5-Bis(trifluoromethyl)phenyl)ethoxy)-3-(S)-(4-fluorophenyl)-4-(phthalamidoethyl)morpholine A solution of the compound of Description 5 (606 mg), N-(2-bromoethyl)phthalimide, sodium hydrogen carbonate (350 mg) and sodium iodide (50 mg) in dry acetonitrile were heated at reflux under an atmosphere of argon. The mixture was cooled and dispersed between ethyl acetate and water. The organic extract was washed with brine, dried (MgSO$_4$) and evaporated. The residue was purified by chromatography on silica using 2% methanol in dichloromethane as eluant. The product was further purified by recrystallisation from petrol to afford colourless prisms (594 mg): mp 140.5°–141.5° C.
(b) 4-(2-Aminoethyl)-2-(R)-(1-(R)-(3,5-bis(trifluoromethyl) phenyl)ethoxy)-3-(S)-(4-fluorophenyl)morpholine The phthalimide of (a) above (429 mg) was dissolved in methanol (0.5 ml) and dichloromethane (0.5 ml). Hydrazine hydrate (100 ml) was added and the resulting mixture was stirred at room temperature for 24 hours, during which time a white solid precipitated. The mixture was diluted with ethyl acetate and the solid phthalazide byproduct was removed by filtration. The filtrate was extracted into hydrochloric acid (2N) and after the emulsion had separated the acidic layer was removed and made basic with aqueous sodium carbonate solution. This mixture was extracted with ethyl acetate (3×10 ml), the organic extracts were dried (K$_2$CO$_3$), filtered and evaporated. The residue was treated with ethereal hydrogen chloride to afford the product as the dihydrochloride salt. Anal. Calcd. for C$_{22}$H$_{23}$F$_7$N$_2$O$_2$.2HCl: C, 48.64: H, 3.93: N, 6.13. found: C, 48.71; H, 3.99; N, 6.27%. MS (CI$^+$) m/z 481 (M$^+$+1, 100% ).

EXAMPLE 2

2-(R)-(1-(R)-(3.5-Bis(trifluoromethyl)phenyl)ethoxv)-3-(S) -(4-fluorophenyl)-4-(2-pyrrolidinoethyl)morpholine
(a) 2-(R)-(1-(R)-(3,5-Bis(trifluoromethyl)phenyl)ethoxy)-4-carbomethoxymethyl)-3-(S)-(4-fluorophenyl)morpholine.

To the compound of Description 5 (1.1 g) in dry dimethylformamide (5 ml) was added caesium carbonate (1.64 g) followed by methyl bromoacetate (404 mg). The mixture was stirred at room temperature overnight. The mixture was dispersed between ethyl acetate and water. The organic extract was washed with brine, dried (MgSO$_4$) and evaporated. The residue was purified by chromatography on silica using 30% ether in petrol as eluent to afford the title compound as a colourless oil (1.16g, 90%). This was used in the next step without further purification.
(b) 2-(R)-(1-(R)-(3,5-Bis(trifluoromethyl)phenyl)ethoxy)-3-(S)-(4-fluorophenyl)-4-(formylmethyl)morpholine.

To the ester (1.16 g) described in (a) above, in dry dichloromethane (2.5 ml) at −78° C. was added dropwise with stirring a relation of diisobutylaluminium hydride (2.4 ml, 1.0M in toluene) over 2h. The mixture was stirred at −78° C. for 24 hours and quenched at this temperature by the addition of saturated aqueous ammonium chloride. The mixture was partitioned between dichloromethane and citric acid (10% aqueous). The organic layer was dried (Na$_2$SO$_4$) and evaporated to afford a pale yellow oil (976 mg, 89%) which was used in the next step without further purification.
(c) 2-(R)-(1-(R)-(3,5-Bis(trifluoromethyl)phenyl)ethoxy)3-(S)-(4-fluorophenyl)-4-(2-(2-pyrrolidinoethyl)morpholine The aldehyde (141 mg) described in (b) above was dissolved in dichloromethane (2 ml). Magnesium sulfate (500 mg) was added with stirring followed by pyrrolidine (200 μl). The mixture was stirred at room temperature overnight and then filtered and evaporated. The residue borohydride was added and the mixture was stirred for 2 hours. The mixture was diluted with ethyl acetate and the resulting solution was washed with water and brine. The organic phase was dried (MgSO$_4$) and evaporated. The residue was purified by chromatograhy on alumina (grade III) using 0.5% methanol in dichloromethane as eluent. The product was treated with ethereal hydrogen chloride and he resulting dihydrochloride salt was recrystallised from ethyl acetate to afford a white crystallise substance (40mg): mp 205°–207° C. Anal. Calcd. for C$_{26}$H$_{29}$F$_7$N$_2$O$_2$. 2HCl: C, 51.41; H, 5.14; N, 4.61. Found: C, 50.90; H, 5.12; N, 4.16%. MS (CI$^+$) m/z 535 (M$^+$+1, 50%).

EXAMPLE 3

2-(R)-(1-(R)-(3,5-Bis(trifluoromethyl)phenyl)ethoxy)-3-(S) -(4-fluorophenyl)-4-(2-morpholinoethyl)morpholine To the compound of Example 1 (74 mg) in dry acetonitrile (2 ml) was added sodium hydrogen carbonate (500 mg) and 2-bromoethyl ether (125 ml). The mixture was stirred at room temperature for 24 hours and was partitioned between water and ethyl acetate. The organic layer was dried (MgSO$_4$) and evaporated and the residue was purified by chromatography on alumina (grade III) using dichloromethane as eluant. The free base was treated with ethereal hydrogen chloride and the resulting dihydrochloride salt was recrystallised from dichloromethane/ethyl acetate to afford white crystals: mp 188°–190° C. Anal. Calcd. for C$_{26}$H$_{29}$F$_7$N$_2$O$_3$.2HCl. ½ H$_2$O: C, 49.38; H, 5.10; N, 4.43%. MS (CI$^+$) m/z 551 (M$^+$+1, 100%).

EXAMPLE 4

2-(R)-(1-(R)-(3,5-Bis(trifluoromethyl)phenyl)ethoxy)-4-(2-(2'-(S)-carboxypyrrolidino)ethyl)-3-(S)-(4-fluorophenyl) morpholine To the aldehyde (128 mg) described in Example 2 (b) in dry dimethylformamide (1 ml) was added L-proline benzyl ester hydrochloride followed by sodium cyanoborohydride (126 mg). The mixture was stirred at room temperature overnight and then diluted with water. This mixture was extracted with ethyl acetate and the organic extract was dried (MgSO$_4$) and evaporated. The residue was purified by chromatography on silica using 2% methanol in dichloromethane as eluent. This intermediate benzyl ester was dissolved in ethyl acetate and hydrogenated at atmospheric pressure in the presence of palladium on charcoal as catalyst for 2h. The catalyst was removed by filtration and the residue treated with ethereal hydrogen chloride. The resulting dihydrochloride salt was recrystallised from hot ethyl acetate/diethyl ether to afford a crystalline solid: mp 157°–160° C. MS (CI$^+$) m/z 579 (M$^+$+1, 70%).

EXAMPLE 5

2-(R)-(1-(R)-(3,5-Bis(trifluoromethyl)phenyl)ethoxy)-3-(S)-(4-fluorophenyl)-4-(2-(2'-(R)-hydroxymethylpyrrolidino)ethyl)morpholine The aldehyde of Example 2(b) (113 mg) was reacted with (R)-2-pyrrolidinemethanol according to the conditions described in Example 2 (c) to afford the product as the dihydrochloride salt. $^1$H NMR (360 MHz, D$_2$O) δ 1.61 (3H, d, J=6.5 Hz), 1.8–1.91 (1H, m), 1.99–2.16 (2H, m x 2), 2.23–2.31 (1H, m), 3.00–3.06 (2H, m), 3.21 (1H, inc), 3.30–3.36 (1H, m), 3.44 (1H, inc), 3.53–3.56 (1H, inc), 3.62–3.72 (2H, m), 3.77–3.90 (2H, m), 3.97 (1H, dd, J=12.5, 3.0 Hz), 4.04 (1H, d, J=10.0 Hz), 4.23 (1H, s), 4.48 (1H, t, J=12.0 Hz), 4.67 (1H, s), 4.84 (1H, d, J=4.0 Hz), 5.05 (1H, q, J=6.0 Hz), 7.23 (2H, t, J=8.0 Hz), 7.52 (4H, br s), 7.82 (1H, s, Axil). MS (CI$^+$) m/z 565 (M$^+$+1, 100%).

EXAMPLE 6

2-(R)-(1-(R)-(3,5-Bis(trifluoromethyphenyl)ethoxv)-4-(2-(4'-carbomethoxy-2'-oxopyrrolidino)ethyl)-3-(S)-(4-fluorophenyl)morpholine (Isomers A and B)

To the amine (98 mg) described in Example 1 (c) was added dimethyl itaconate (90 mg) and methanol. The resulting mixture was heated at reflux for 24h and was then evaporated. The residue was purified by chromatography on silica using 2% methanol in dichloromethane as eluent. This afforded a mixture of diastereoisomers (1:1) as a colourless oil. This was treated with ethereal hyrogen chloride and the resulting hydrochloride salt was recrystallised from ethyl acetate/diethyl ether to afford the product as a crystalline solid: mp 156°–158° C. MS (ES) m/z 607 (M$^+$+1, 100%).

EXAMPLE 7

2-(R)-(1-(R)-3,5-Bis(trifluoromethyl)phenyl)ethoxy)-4-(2-(N'-carboethoxy)guanidino)ethyl)-3-(S)-(4-fluorophenyl) morpholine To the compound of Example 1 (800 mg) was added N,N'-di-t-butoxy-S-methylisothiourea (507 mg) in ethanol (10 ml) and the resulting mixture was heated at reflux for 5h. The methyl mercaptan byproduct was scavenged using a bleach trap in line. The solvent was removed in vacuo and the residue was purified by column chromatography on silica using 20% ethyl acetate in petrol as eluent (340 mg). This was treated with trifluoroacetic acid in dichloromethane for 3h and the mixture was concentrated in vacuo. The residue was dispersed between diethyl ether and water containing 1,1,3,3-tetramethylguanidine. The organic extract was separated, dried (MgSO$_4$) and evaporated to afford the free base which was purified by chromatography on silica using 5% methanol in dichloromethane as the eluent. This was treated with ethereal hydrogen chloride to give the dihydrochloride salt as a white solid (220 mg). Anal. Calcd. for C$_{26}$H$_{29}$F$_7$N$_4$O$_4$.2HCl.1.2H$_2$O: C, 45.32; H, 4.88; N, 8.13. Found: C, 45.08; H, 4.52; N, 7.79%. MS (ES) m/z 595 (M$^+$+1, 100%).

EXAMPLE 8

2-(R)-1-(R)-(3,5-Bis(trifluoromethyl)phenyl)ethoxy)-3-(S)-phenyl-4-2-4-phenylpiperidino)ethyl)morpholine To a solution of the compound of Description 10 (50 mg) and 1-(2-chloroethyl)-4-phenylpiperidine hydrochloride (50 mg) in acetonitrile (1 ml) was added diisopropylethylamine (0.1 ml) and tetrabutylammoninm iodide (catalytic). The mixture was heated at 50° C. for 4 days and then was concentrated in vacuo. The residue was purified on silica gel using ethyl acetate/hexane/triethylamine (78:20:2) as eluent to afford the title compound (42 mg). $^1$H NMR (CDCl$_3$) δ 1.43 (3H, d, J=6.6 Hz), 1.65–1.80 (4H, m), 1.90–2.05 (2H, m), 2.05–2.15 (1H, m), 2.40–2.60 (4H, m), 2.75–2.85 (1H, m), 2.88 (2H, br t, J=12 Hz), 3.11 (1H, d, J =12Hz), 3.40 (d, J=2.8 Hz), 3.65 (1H, br dd, J=2.0 and 11 Hz), 4.28 (1H, dt, J =2.2 and 11 Hz), 4.31 (1H, d, J=2.9 Hz), 4.82 (1H, q, J=6.6 Hz), 7.10–7.40 (10H, m), 7.34 (2H, s), 7.58 (1H, s).

EXAMPLE 9

3-(S)-Phenyl-4(2-(4-phenylpiperidino)ethyl-2-(R)-1-(R)-3-trifluoromethyl)phenyl)ethoxy)morpholine The compound of Description 11 was reacted according to the procedure described in Example 8 to afford the title compound as a colourless oil. NMR (CDCl$_3$) δ 1.39 (3H, d, J=6.6 Hz), 1.65–1.80 (4H, m), 1.90–2.05 (2H, m), 2.05–2.15 (1H, m), 2.40–2.60 (4H, m), 2.75–2.85 (1H, m), 2.88 (2H, br t, J=12 Hz), 3.11 (1H, d, J=12 Hz), 3.39 (d, J=2.8 Hz), 3.65 (1H, br dd, J=2.0 and 11 Hz), 4.30 (1H, d, J=2.9 Hz), 4.31 (1H, dt, J=2.2 and 11 Hz), 4.74 (1H, q, J=6.6 Hz), 6.56 (1H, d, J=7.8 Hz), 6.95 (1H, s), 7.03 (1H, t, J=7.8 Hz), 7.10–7.20 (3H, m), 7.20–7.40 (8H, m).

EXAMPLE 10

2-(R)-(1-(R)-(3-Fluoro-5-(trifluoromethyl)phenyl)ethoxy)-3-(S)-phenyl-4-(2-(spiro(indene-3,4-piperidino))ethyl) morpholine The compound of Description 12 was reacted with 1-(2-chloroethyl)spiro(indene-3',4-piperidine) hydrochloride according to the procedure described in Example 8 to afford the tide compound as a colourless oil. NMR (CDC$_3$) δ 1.38 (3H, d, J=6.6 Hz), 2.10–2.20 (2H, m), 2.20–2.30 (3H, m), 2.55 (2H, br dt, J=3.5 and 12 Hz), 2.55–2.70 (1H, m), 2.80–2.95 (3H, m), 3.13 (1H, d, J=12 Hz), 3.43 (d, J=2.9 Hz), 3.60–3.70 (1H, m), 4.29 (1H, dt, J=2.5 and 12 Hz), 4.30 (1H, d, J=2.9Hz), 4.74 (1H, q, J=6.6 Hz), 6.16 (1H, d, J=9.2

Hz), 6.70 (1H, d, J=5.6 Hz), 6.77 (1H, d, J=45.6 Hz), 6.80 (1H, s), 7.00 (1H, d, J=8.1 Hz), 7.10–7.40 (9H, m

EXAMPLE 11

2-(R)-(1-(R)-(3-Fluoro-5-(trifluoromethyl)phenyl)ethoxy)-3-(S)-phenyl-4-(2-(4-phenylpiperidino)ethyl)morpholine The compound of Description 12 was reacted according to the procedure described in Example 8 to afford the title compound as an oil. NMR (CDCl$_3$) δ 1.38 (3H, d, J=6.6 Hz), 1.65–1.80 (4H, m), 1.90–2.05 (2H, m), 2.05–2.15 (1H, m), 2.40–2.60 (4H, m), 2.75–2.85 (1H, m), 2.88 (2H, br t, J=12 Hz), 3.11 (1H, d, J=12 Hz), 3.41 (d, J=2.9 Hz), 3.64 (1H, br dd, J=2.5 and 11 Hz), 4.28 (1H, dt, J=2.5 and 11 Hz), 4.30 (1H, d, J=2.9 Hz), 4.73 (1H, q, J=6.6 Hz), 6.15 (1H, d, J=10.2 Hz), 6.80 (1H, s), 7.08 (1H, d, J=10.2 Hz), 7.10–7.20 (3H, m), 7.24 (2H, d, J=7.7 Hz), 7.25–7.35 (5H, m).

EXAMPLE 12

2-(R)-(1-(R)-(3-Fluoro-5-(trifluoromethyl)phenyl)ethoxy)-4-(2-(1'-methylsulfonyl-spiro(indoline-3',4-piperidino))ethyl)-3-(S)-phenylmorpholine The compound of Description 12 was reacted with 1-(2-chloroethyl)-1'-methylsulfonyl-spiro(indoline-3',4-piperidine) hydrochloride following the procedure described in Example 8 to afford the title compound as an oil. NMR (CDCl$_3$) δ 1.38 (3H, d, J=6.6 Hz), 1.55–1.65 (2H, m), 1.90–2.05 (4H, m), 2.05–2.15 (1H, m), 2.40–2.60 (4H, m), 2.75–2.85 (3H, m), 2.86 (3H, s), 3.10 (1H, d, J=12 Hz), 3.40 (d, J=2.9 Hz), 3.65 (1H, br dd, J=2.5 and 12 Hz), 3.73 (2H, s), 4.28 (1H, dt, J=2.5 and 12 Hz), 4.30 (1H, d, J=2.9 Hz), 4.73 (1H, q, J=6.6 Hz), 6.15 (1H, d, J=9.4 Hz), 6.80 (1H, s), 6.95–7.05 (2H, m), 7.15–7.25 (2H, m), 7.25–7.40 (6H, m).

EXAMPLE 13

2 -(R)-(1-(R)-(3-Fluoro-5-(trifluoromethyl)phenyl)ethoxy)-3-(S)-phenyl-4-(2-piperidinoethyl)morpholine The compound of Description 12 was reacted with 1-(2-chloroethyl)piperidine hydrochloride according to the procedure described in Example 8 to afford the title compound as an oil. NMR (CDCl$_3$) δ 1.37 (3H, d, J=6.6 Hz), 1.45–1.60 (4H, m), 2.00–2.10 (1H, m), 2.10–2.40 (7H, m), 2.40–2.55 (2H, m), 2.75–2.85 (1H, m), 3.10 (1H, d, J=12 Hz), 3.37 (d, J=2.9 Hz), 3.61 (1H, br dd, J=2.5 and 11 Hz), 4.26 (1H, dt, J=2.5 and 11 Hz), 4.28 (1H, d, J=2.9 Hz), 4.72 (1H, q, J=6.6 Hz), 6.15 (1H, d, J =9.2 Hz), 6.79 (1H, s), 6.99 (1H, d, J=8.4 Hz), 7.25–7.35 (5H, m).

EXAMPLE 14

2-(S)-(3,5-Bis(trifluoromethyl)phenyl)methyloxy-3-(S)-phenyl-4-(2-(4-phenylpiperidino)ethyl)morpholine The compound of Description 7 was reacted according to the procedure described in Example 8 to afford the title compound as an oil. NMR (CDCl$_3$) δ 1.60–1.80 (4H, m), 1.90–2.05 (2H, m), 2.05–2.20 (1H, m), 2.35–4.10 (1H, m), 2.75–2.95 (3H, m), 3.13 (1H, d, J=11.6 Hz), 3.52 (1H, d, J=2.6 Hz), 3.70 (1H, 2 m), 4.19 (dr, J=2.3 and 11.6 Hz), 4.10 (1H, d, J=3.6 Hz), 4.63 (1H, d, J=2.6 Hz), 4.77 (1H, d, J=13.3 Hz), 7.16 (2H, d, J=7.3 Hz), 7.20–7.35 (6H, m), 7.35–7.45 (4H, m), 7.67 (1H, s).

EXAMPLE 15

4-(2-(4-Benzylpiperidino)ethyl)-2-(S)-(3,5-bis(trifluoromethyl)phenyl)methyloxy-3 -(S)-phenylmorpholine The compound of Description 6 was reacted with 1-(2-chloroethyl)-4-benzylpiperidine hydrochloride according to the procedure described in Example 8 to afford the title compound as an oil. $^1$H NMR (CDCl$_3$) δ 1.10–1.35 (2H, m), 1.35–1.60 (4H, m), 1.60–2.00 (3H, m), 2.05–2.25 (1H, m), 2.35–2.65 (3H, m), 2.45 (2H, d, J=7 Hz), 2.65–2.95 (2H, m), 3.09 (1H, d, J=1.6 Hz), 3.50 (1H, d, J=2.6 Hz), 3.66 (1H, 2 br d), 4.15 (dr, J=2.3 and 11.6 Hz), 4.38 (1H, d, J=13.6 Hz), 4.61 (1H, d, J=2.6 Hz), 4.75 (1H, d, J=3.3 Hz), 7.06 (2H, d, J=7.5 Hz), 7.14 (1H, t, J=7.5 Hz), 7.20–7.35 (5H, m), 7.37 (4H, br s), 7.67 (1H, s).

We claim:

1. A compound of the formula (I):

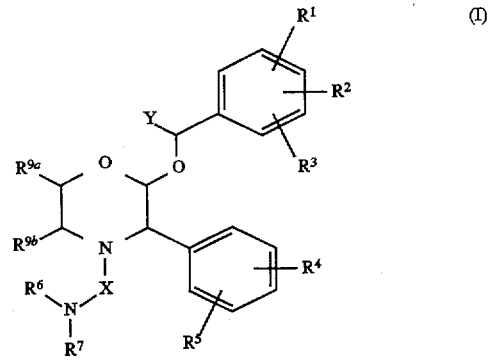

wherein

R$^1$ is hydrogen, halogen, C$_{1-6}$alkyl, C$_{1-6}$alkoxy, CF$_3$, NO$_2$, CN, CO$_2$R$^a$, CONR$^a$R$^b$, C$_{2-6}$alkenyl, C$_{2-6}$alkynyl or C$_{1-4}$alkyl substituted by C$_{1-4}$alkoxy, and wherein R$^a$ and R$^b$ are each independently hydrogen or C$_{1-4}$alkyl;

R$^2$ is hydrogen, halogen, C$_{1-6}$alkyl, C$_{1-6}$alkoxy substituted by C$_{1-4}$alkoxy or CF$_3$;

R$^3$ is hydrogen, halogen or CF$_3$;

R$^4$ is hydrogen, halogen, C$_{1-6}$alkyl, C$_{1-6}$alkoxy, hydroxy, CF$_3$, NO$_2$, CN, CO$_2$R$^a$, CONR$^a$R$^b$, C$_{2-6}$alkenyl, C$_{2-6}$alkynyl or C$_{1-4}$alkyl substituted by C$_{1-4}$alkoxy, wherein R$^a$ and R$^b$ are as previously defined;

R$^5$ is hydrogen, halogen, C$_{1-6}$alkyl, C$_{1-6}$alkoxy substituted by C$_{1-4}$alkoxy or CF$_3$;

R$^6$ and R$^7$, together with the nitrogen atom to which they are attached, form a saturated heterocyclic ring of 4 to 7 ring atoms which may optionally contain in the ring one oxygen or sulphur atom or a group selected from NR$^8$, S(O) or S(O)$_2$ and which ring may be optionally substituted by one or two groups selected from phenyl, hydroxyC$_{1-4}$alkyl, C$_{1-4}$alkoxyC$_{1-4}$alkyl, hydroxy, oxo, COR$^a$ or CO$_2$R$^a$ where R$^a$ is as previously defined;

or R$^6$ and R$^7$, together with the nitrogen atom to which they are attached, form a piperidino ring substituted by a spiro-fused indene or indoline group, each of which may be unsubstituted or substituted on any available carbon atom by a group selected from C$_{1-6}$alkyl, C$_{1-6}$alkoxy, hydroxy, halogen, cyano, trifluoromethyl, SO$_2$C$_{1-6}$alkyl, NR$^a$R$^b$, NR$^a$COR$^b$ or CONR$^a$R$^b$; or, in the case of an indoline group, on the nitrogen atom by a group selected from C$_{1-6}$alkyl, C$_{3-7}$cycloalkyl, C$_{3-7}$cycloalkylC$_{1-4}$alkyl; phenylC$_{1-4}$alkyl, CO$_2$R$^a$, CONR$^a$R$^b$, SOR$^a$, or SO$_2$R$^a$, where R$^a$ and R$^b$ are as previously defined;

R$^8$ is hydrogen, C$_{1-4}$alkyl, hydroxyC$_{1-4}$-alkyl or C$_{1-4}$alkoxyC$_{1-4}$alkyl;

R$^{9a}$ and R$^{9b}$ are each independently hydrogen or C$_{1-4}$alkyl, or R$^{9a}$ and R$^{9b}$ are joined so, together with the carbon atoms to which they are attached, there is formed a $C_{5-7}$ ring;

X is selected from —$CH_2CH_2$—, —$COCH_2$— or —$CH_2CO$—; and

Y is $C_{1-4}$alkyl optionally substituted by a hydroxyl group; or a pharmaceutically acceptable salt thereof.

2. A compound as claimed in claim 1 wherein $R^4$ is hydrogen, halogen, $C_{1-6}$alkyl, $C_{1-6}$alkoxy, $CF_3$, $NO_2$, CN, $CO_2R^a$, $CONR^aR^b$, $C_{2-6}$alkenyl, $C_{2-6}$alkynyl or $C_{1-4}$alkyl substituted by $C_{1-4}$alkoxy, and wherein $R^a$ and $R^b$ are each independently hydrogen or $C_{1-4}$alkyl.

3. A compound as claimed in claim 1 of the formula (Ia):

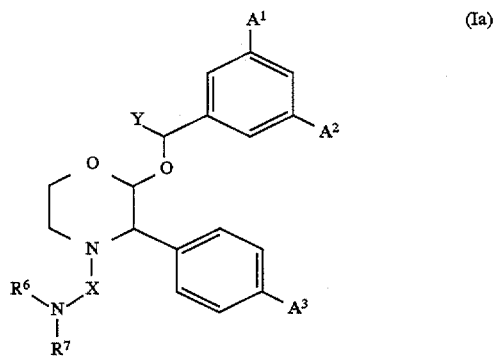

wherein $A^1$ is hydrogen, fluorine or $CF_3$;

$A^2$ is fluorine or $CF_3$;

$A^3$ is fluorine or hydrogen;

and X, Y, $R^6$ and $R^7$ are as defined in claim 1;

or a pharmaceutically acceptable salt thereof.

4. A compound as claimed in claim 1 of the formula (Ib):

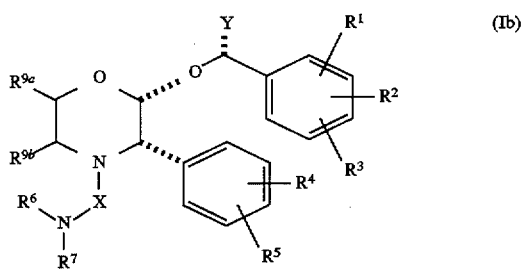

wherein $R^1$, $R^2$, $R^3$, $R^4$, $R^5$, $R^6$, $R^7$, $R^{9a}$, $R^{9b}$, X and Y are as previously defined;

or a pharmaceutically acceptable salt thereof.

5. A compound as claimed in claim 1 wherein $R^6$ and $R^7$, together with the nitrogen atom to which they are attached, form a saturated heterocyclic ring of 4 to 7 ring atoms which may optionally contain in the ring one oxygen or sulphur atom or a group selected from $NR^8$, S(O) or $S(O)_2$ and which ring may be optionally substituted by phenyl, hydroxy$C_{1-4}$alkyl, $C_{1-4}$alkoxy$C_{1-4}$alkyl, hydroxy, oxo, $COR^a$ or $CO_2R^a$, or wherein $R^6$ and $R^7$, together with the nitrogen atom to which they are attached, form a piperidino ring substituted by a spiro-fused indene or indoline group which may be unsubstituted or substituted as defined in claim 1.

6. A compound as claimed in claim 5 wherein $R^6$ and $R^7$, together with the nitrogen atom to which they are attached, form a saturated heterocyclic ring of 5 or 6 ring atoms which may optionally contain in the ring one oxygen atom and which ring may be optionally substituted by phenyl, hydroxy$C_{1-4}$alkyl, oxo or $CO_2R^a$, or wherein $R^6$ and $R^7$, together with the nitrogen atom to which they are attached, form a piperidino ring substituted by a spiro-fused indene or indoline group which may be unsubstituted or, in the case of an idoline group, substituted on the nitrogen atom by the group $SO_2R^a$.

7. A compound as claimed in claim 1 wherein the group $NR^6R^7$ represents $NH_2$, $NHCH_3$, $N(CH_3)_2$, NHC (=$NCO_2R^a$)$NH_2$, morpholino or optionally substituted pyrrolidino or piperidino.

8. A compound as claimed in claim 1 wherein X is —$CH_2CH_2$—, or —$COCH_2$— where the carbonyl moiety is adjacent to the morpholine ring shown in formula (I).

9. A compound a claimed in claim 1 wherein Y is a methyl or $CH_2OH$ group.

10. A compound selected from:

2-(R)-(1-(R)-(3,5-bis(trifluoromethyl)phenyl)ethoxy)-3-(S)-(4-fluorophenyl)-4-(2-pyrrolidinoethyl)morpholine;

2-(R)-(1-(R)-(3,5-bis(trifluoromethyl)phenyl)ethoxy)-3-(S)-(4-fluorophenyl)-4-(2-morpholinoethyl)morpholine;

2-(R)-(1-(R)-(3,5-bis(trifluoromethyl)phenyl)ethoxy)-4-(2-(2'-(S)-carboxypyrrolidino)ethyl)-3-(S)-(4-fluorophenyl)morpholine;

2-(R)-(1-(R)-(3,5-bis(trifluoromethyl)phenyl)ethoxy)-3-(S)-(4-fluorophenyl)-4-(2-(2'-(R)-hydroxymethylpyrrolidino)ethyl)morpholine;

2-(R)-(1-(R)-(3,5-bis(trifluoromethyl)phenyl)ethoxy)-4-(2-(4'-carbomethoxy-2'-oxopyrrolidino)ethyl)-3-(S)-(4-fluorophenyl)morpholine;

2-(R)-(1-(R)-(3,5-bis(trifluoromethyl)phenyl)ethoxy)-3-(S)-phenyl-4-(2-(4-phenylpiperidino)ethyl)morpholine;

3-(S)-phenyl-4-(2-(4-phenylpiperidino)ethyl)-2-(R)-(1-(R)-(3-(trifluoromethyl)phenyl)ethoxy)morpholine;

2-(R)-(1-(R)-(3-fluoro-5-(trifluoromethyl)phenyl)ethoxy)-3-(S)-phenyl-4-(2-(spiro(indene-3',4-piperidino))ethyl)morpholine;

2-(R)-(1-(R)-(3-fluoro-5-(trifluoromethyl)phenyl)ethoxy)-3-(S)-phenyl-4-(2-(4-phenylpiperidino)ethyl)morpholine;

2-(R)-(1-(R)-(3-fluoro-5-(trifluoromethyl)phenyl)ethoxy)-4-(2-(1'-methylsulfonyl-spiro(indoline-3',4-piperidino))ethyl)-3-(S)-phenylmorpholine;

2-(R)-(1-(R)-(3-fluoro-5-(trifluoromethyl)phenyl)ethoxy)-3-(S)-phenyl-4-(2-(4-piperidino)ethyl)morpholine;

2-(S)-(3,5-bis(trifluoromethyl)phenyl)methyloxy)-3-(S)-phenyl-4-(2-(4-phenylpiperidino)ethyl)morpholine;

or a pharmaceutically acceptable salt thereof.

11. A pharmaceutical composition comprising a compound as claimed in claim 1 in association with a pharmaceutically acceptable carrier or excipient.

12. A method for the treatment or prevention of physiological disorders associated with an excess of tachykinins, which method comprises administration to a patient in need thereof of a tachykinin reducing amount of a compound according to claim 1, or a pharmaceutically acceptable salt thereof.

13. A method according to claim 12 for the treatment or prevention of pain or inflammation.

14. A method according to claim 12 for the treatment or prevention of migraine.

15. A method according to claim 12 for the treatment or prevention of emesis.

* * * * *